United States Patent
Groves

(10) Patent No.: US 8,334,377 B2
(45) Date of Patent: Dec. 18, 2012

(54) PORPHYRIN CATALYSTS AND METHODS OF USE THEREOF

(75) Inventor: John T. Groves, Princeton, NJ (US)

(73) Assignee: The Trustees of Princeton University, Princeton, NJ (US)

( * ) Notice: Subject to any disclaimer, the term of this patent is extended or adjusted under 35 U.S.C. 154(b) by 481 days.

(21) Appl. No.: 12/311,639

(22) PCT Filed: Oct. 5, 2007

(86) PCT No.: PCT/US2007/021453
§ 371 (c)(1),
(2), (4) Date: Feb. 12, 2010

(87) PCT Pub. No.: WO2008/045358
PCT Pub. Date: Apr. 17, 2008

(65) Prior Publication Data
US 2011/0306584 A1    Dec. 15, 2011

Related U.S. Application Data

(60) Provisional application No. 60/850,228, filed on Oct. 6, 2006.

(51) Int. Cl.
*C07D 487/22* (2006.01)
(52) U.S. Cl. .................................. 540/145
(58) Field of Classification Search ............ 540/145
See application file for complete search history.

(56) References Cited

FOREIGN PATENT DOCUMENTS

| WO | WO-0075144 A2 | 12/2000 |
|---|---|---|
| WO | WO-2005077269 A1 | 8/2005 |

OTHER PUBLICATIONS

Batinić-Haberle et al. "New Class of Potent Catalyst of $O_2$ Dismutation." *Dalton Trans.* 33.11(2004):1696-1702.
Batinić-Haberle et al. "New PEG-ylated Mn(III) Porphyrins Approaching Catalytic Activity of SOD Enzyme." *Dalton Trans.* 35.4(2006):617-624.
Okado-Matsumoto et al. "Complementation of SOD-Deficient *Escherichia coli* by Manganese Porphyrin Mimics of Superoxide Dismutase Activity." *Free Radical Bio. Med.* 37.3(2004):401-410.

*Primary Examiner* — Brian McDowell
(74) *Attorney, Agent, or Firm* — Occhiuti Rohlicek & Tsao LLP

(57) ABSTRACT

This invention provides a novel class of substituted macrocyclic metallic compounds. The compounds are useful as peroxynitrite decomposition catalysts. Pharmaceutical compositions, and methods of making and using the compounds, or a pharmaceutically acceptable salt, hydrate, or prodrug thereof are also described.

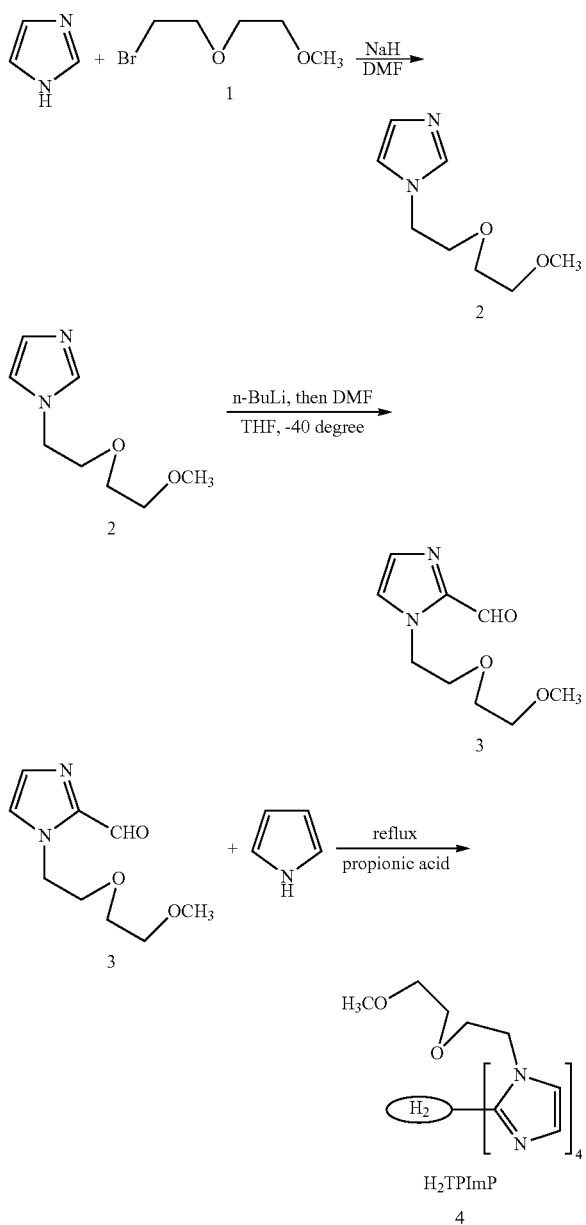

1 Claim, 6 Drawing Sheets

R = A, B, C, D = :

-(CH$_2$)$_n$-X where n=1 to 6 and X = -COOH; -CONH$_2$; -CONR$_2$; -O-PO$_3$H$_2$; -PO$_3$H$_2$; -SO$_3$H; -NH$_2$; -NR$_2$; -NR$_3^+$ -(CH$_2$)$_n$-Y where n = 2 to 6 and Y = -OH; -(-O-(CH$_2$)$_2$)$_m$- Y; m= 1 - 200

-(-O-(CH$_2$)$_2$)$_m$- X where m = 1 - 200 and X = as defined above

1.

Y$_2$ = -(CH$_2$)$_n$O-; -(CH$_2$)$_n$NH-; -(CH$_2$)$_n$S-

2.

3.

4.

5.

R = A, B, C, D = :

6.

7.

A

B

PORPHYRIN CATALYSTS AND METHODS OF USE THEREOF

This is a U.S. national stage application, filed under 35 U.S.C. 371, of International Application PCT/US2007/021453, filed Oct. 5, 2007, which claims priority to U.S. provisional application Ser. No. 60/850,228, filed Oct. 6, 2006.

STATEMENT AS TO FEDERALLY SPONSORED RESEARCH

This invention was made with U.S. Government support under NIH Grant GM 36298 awarded by the National Institutes of Health. The government has certain rights in the invention.

FIELD OF THE INVENTION

The invention relates in general to substituted porphyrin compounds.

BACKGROUND OF THE INVENTION

The peroxynitrite ion ($ONOO^-$) is a potent oxidant formed by the combination of nitric oxide (NO) and the superoxide anion ($O_2$)$^-$. NO has been shown to be generated by numerous cell types, such as macrophages, neutrophils, hepatocytes and endothelial cells. The direct combination of NO with $O_2$ produces the peroxynitrite ion ($ONOO^-$), which decomposes rapidly under physiological conditions to oxidizing intermediates. These oxidizing intermediates can damage biological targets.

Pathological consequences associated with damage to biological targets can include the oxidizing or nitrating of proteins, lipids and DNA. $ONOO^-$ crosses lipid membranes at a rate significantly faster than the rates of other known oxidants, indicating that this oxidant can travel distances of cellular dimensions. Thus, even in the presence of biological membranes, $ONOO^-$ can have free access to cellular interiors. $ONOO^-$ is also known to nitrate tyrosine residues in proteins, and to oxidize sulfhydryls, methionines and macromolecules such as, for example, metalloenzymes, DNA, and lipids.

In light of this reactivity, $ONOO^-$ has been implicated in a variety of diseases. These diseases include, e.g., neurodegenerative disorders such as Alzheimer's disease, amyotrophic lateral sclerosis, stroke, AIDS dementia and Huntington's disease; heart diseases such as atherosclerosis; chronic inflammation and autoimmune diseases such as arthritis, inflammatory bowel disease, and acute respiratory disease syndrome; cancer; ischemic-reperfusion injury; septic shock; and chronic rejection of renal grafts.

SUMMARY OF THE INVENTION

The invention is based in part on the discovery of substituted pyridyl- and imidazolyl-porphyrin compounds that are effective peroxynitrite decomposition catalysts. Preferred catalysts have one or more of the properties of high catalytic activity, high stability and enhanced lifetime in the blood pool, advantageous tissue distribution, and low toxicity. The peroxynitrite decomposition catalysts can be used to treat a variety of conditions and diseases, including those known to result from the accumulation of peroxynitrite.

Accordingly, in one aspect the invention provides a novel substituted porphyrin to compound falling within formulae I, II, III, or IV as set forth below:

Formula I

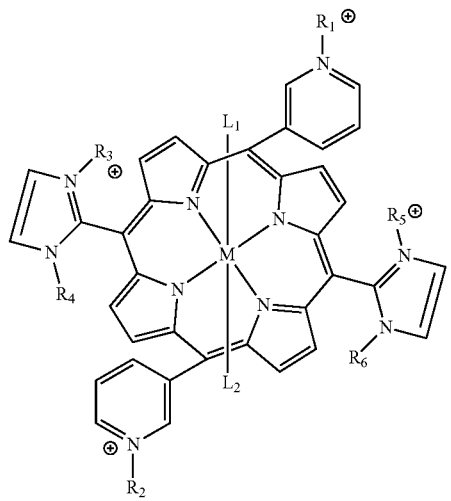

Formula II

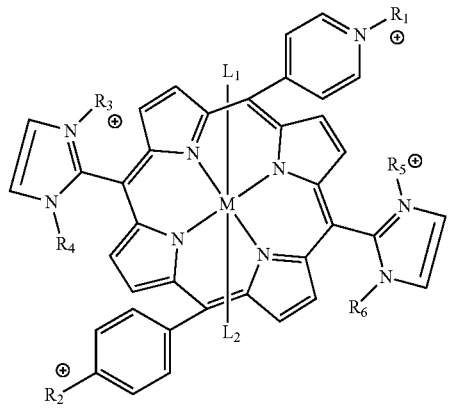

Formula III

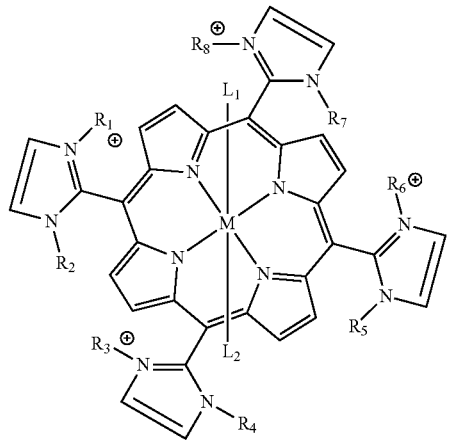

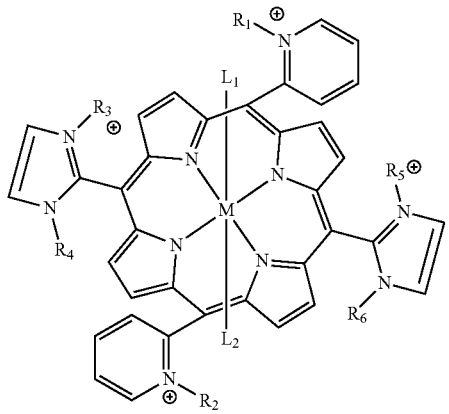

Formula IV or a pharmaceutically acceptable base or acid addition salt, hydrate, ester, solvate, prodrug, metabolite, or stereoisomer, or mixtures thereof, wherein at least one of $R_1$, $R_2$, $R_3$, $R_4$, $R_5$, $R_6$, $R_7$, or $R_8$ is independently selected from a moiety selected from the group consisting of
$CH_2CH_2OCH_3$,
$CH_2CH_2OCH_2CH_2OCH_3$,
$CH_2COO^-$,
$(CH_2)_n$—X,
$(CH_2)_n$—Y,
$(CH_2)_n$Ar—X,
$(CH_2)_n$Ar—Y,
$CH_2CH_2OCH_2CH_2OCH_2CH_2OCH_3$,
$CH_2CO_2CH_2CH_3$,
$(OCH_2CH_2)_m$—X,
$(OCH_2CH_2)_m$—Y,
$Y_2$—X,
$Y_2C(Z_1)_3$,
further wherein: $Z_1$ is $CH_2OCH_2(CH_2)$—X or $CH_2OCH_2(CH_2)_nY$;
$(CH_2)_nC(O)Y_2C(Z_2)_3$,
wherein: $Z_2$ is $CH_2OCH_2CH_2C(O)Y_2C(Z_4)_3$ and $Z_4$ is $CH_2OCH_2CH_2X$;
$(CH_2)_nC(O)$—$Y_2$—$C(Z_5)_3$,
wherein: $Z_5$ is $CH_2OCH_2CH_2C(O)Y_2C(Z_6)_3$ and 4 is $CH_2OCH_2CH_2C(O)O(CH_2CH_2O)_mCH_2CH_2O^-$;
$(CH_2)_nOCH_2C(CH_2OH)_3$,
$(CH_2)_nOCH_2CH(CH_2O)_2$,
$(CH_2)_nOCH_2C(CH_2OH)_2(CH_3)$,
$(CH_2)_nOCH_2C[CH_2OCH_2C(CH_2OH)_3]_3$,
$(CH_2)_nOCH_2C[CH_2OCH_2C(CH_2O[CH_2CH_2O]_mCH_2CH_2OX)_3]_3$,
$CH_2CONH$—Y,
$CH_2CO$—Y, and
$CH_2CO(CH_2)_p$—Y;
wherein n is an integer 1, 2, 3, 4, 5, 6, 7, 8, 9, or 10; m is an integer from 1 to 200, and p is 1 or 2;

X is COOH, COOR', $CONH_2$, CONHR', $CONR'_2$, $CO(CH_2)_pR'$, $OPO_3H_2$, $PO_3H_2$, $SO_3H$, $NH_2$, $NR'_2$, or $NR'_3{}^+$, a steroid, an amino acid, an oligosaccharide, a peptide, or a polycarboxylic acid, further wherein
R' is selected from alkyl, $CH_2CH_2OCH_3$, $CH_2CH_2OCH_2CH_2OCH_3$, $(CH_2)_n$—X, $(CH_2)_n$—Y, $(CH_2)_n$Ar—X, $(CH_2)_n$Ar—Y, $CH_2CH_2OCH_2CH_2OCH_2CH_2OCH_3$, $CH_2CO_2CH_2CH_3$, $(OCH_2CH_2)_m$—X, $(OCH_2CH_2)_m$—Y, $Y_2$—X, $Y_2C(Z_1)_3$, further wherein: $Z_1$ is $CH_2OCH_2(CH_2)_nX$ or $CH_2OCH_2(CH_2)_nY$; $(CH_2)_nC(O)Y_2C(Z_2)_3$, wherein: $Z_2$ is $CH_2OCH_2CH_2C(O)Y_2C(Z_4)_3$ and $Z_4$ is $CH_2OCH_2CH_2X$; $(CH_2)_nC(O)$—$Y_2$—$C(Z_5)_3$, wherein:
$Z_5$ is $CH_2OCH_2CH_2C(O)Y_2C(Z_6)_3$ and $Z_6$ is $CH_2OCH_2CH_2C(O)O(CH_2CH_2O)_mCH_2CH_2O$; $(CH_2)_nOCH_2C(CH_2OH)_3$, $(CH_2)_nOCH_2CH(CH_2OH)_2$, $(CH_2)_nOCH_2C(CH_2OH)_2(CH_3)$, $(CH_2)_nOCH_2C[CH_2OCH_2C(CH_2OH)_3]_3$, $(CH_2)_nOCH_2C[CH_2OCH_2C(CH_2O[CH_2CH_2O]_mCH_2CH_2OX)_3]_3$, $CH_2CONH$—Y, $CH_2CO$—Y, and $CH_2CO(CH_2)_p$—Y;

Y is OH or $(OCH_2CH_2)_m$—$W_1$ or $(CH_2CH_2)_m$—$W_2$; where $W_1$ is OH, or $(OCH_2CH_2)_mOH$ and $W_2$ is OR", further wherein R" is an alkyl;

$Y_2$ is selected from the group consisting of $(CH_2)_nO$, $(CH_2)_nNH$, and $(CH_2)_nS$, $CH_2CONH$, $CH_2COO$, or $CH_2CO(CH_2)_p$; and wherein the remaining $R_1$, $R_2$, $R_3$, $R_4$, $R_5$, $R_6$, $R_7$ or $R_8$ are hydrogen;

Ar is substituted or unsubstituted phenyl or substituted or unsubstituted naphthyl; $L_1$ and $L_2$ are, independently, absent, halide, oxo, $OH_2$, hydroxo, CN, $OPO_3H$ or alcohol; and M is absent, Mn or Fe.

In some embodiments when the compound is Formula III, then $R_1$, $R_2$, $R_3$, $R_4$, $R_5$, $R_6$, $R_7$, and $R_8$ are not all $CH_2CH_2OCH_3$. In further embodiments, if the compound is Formula III, then Ar is not unsubstituted phenyl when n is 1 and X is COOH.

Compounds falling within the formulae include various substituents, e.g., those including one or more linear, dendritic or branched polyethers, such as polyethylene glycol (PEG) moieties; linear, dendritic or branched polycarboxylic acids; oligosaccharides; peptides; steroids; and amino acids.

Also provided are methods of treating Alzheimer's disease, amyotrophic lateral sclerosis, stroke, AIDS dementia, Huntington's disease, atherosclerosis, inflammation, arthritis, neurodegeneration, sepsis, autoimmune diseases, cancer, ischemia-reperfusion injury, septic shock, diabetes, diabetic vascular complications, diabetic cardiomyopathy, diabetic neuropathy, hyperglycemia, pathophysiological conditions of the heart, acute myocardial infarction, chronic ischemic heart failure, doxorubicin-induced cardiac disfunction, oxidative stress, obliterative bronchiolitis, colitis, vascular dysfunction, myocardial dysfunction, myocardial necrosis, and chronic graft in mammals by administering to a mammal in need of such treatment a pharmaceutically effective amount of a compound according to formulae I, II, III, or IV.

Also provided are pharmaceutical compositions including the compounds of the invention and a pharmaceutically acceptable carrier.

In yet another aspect, the invention includes the use of compounds disclosed herein as diagnostic probes to determine the involvement of peroxynitrite and other reactive oxygen and nitrogen species in disease states both in vivo and in vitro.

The details of one or more embodiments of the invention are set forth in the accompanying description below. Although any methods and materials similar or equivalent to those described herein can be used in the practice or testing of the invention, the preferred methods and materials are now described. Other features, objects, and advantages of the invention will be apparent from the description and from the claims. In the specification and the appended claims, the singular forms also include the plural unless the context clearly dictates otherwise. Unless defined otherwise, all technical and scientific terms used herein have the same meaning as commonly understood by one of ordinary skill in the art to which this invention belongs. All patents and publications cited in this specification are incorporated by reference.

DETAILED DESCRIPTION OF THE INVENTION

Figure 1A:
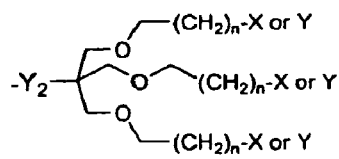
FIGS. 1A and 1B are examples of PEG substituent groups ($R_1$, $R_2$, $R_3$, $R_4$, $R_5$, $R_6$, $R_7$, and $R_8$) for compounds according to the invention.
Figure 1A:
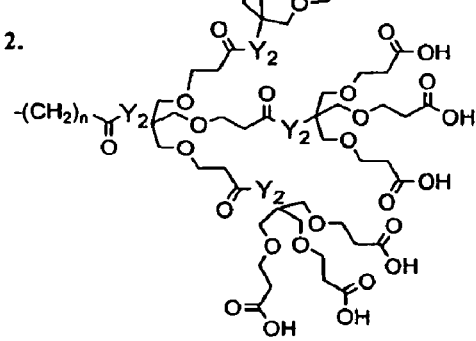
Figure 1A:
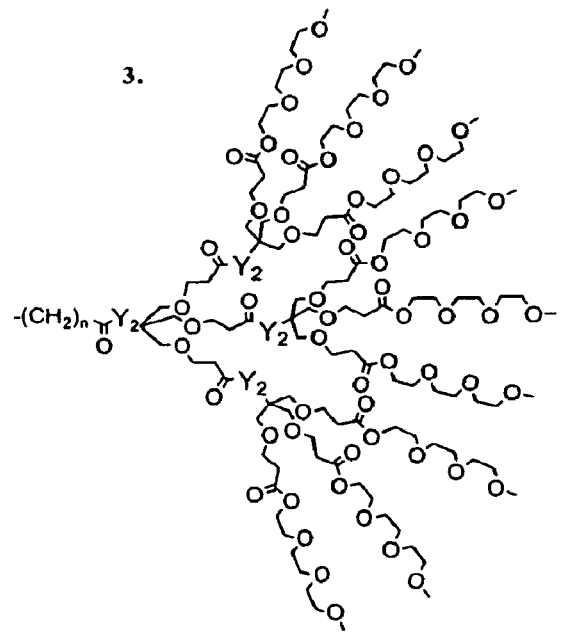
Figure 1A:
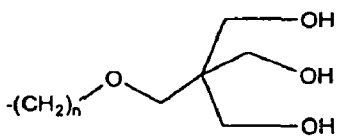
Figure 1A:
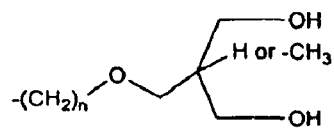

The invention provides novel substituted macrocyclic compounds that can be complexed to a metal to form metallic compounds. The compounds are useful as e.g., peroxynitrite decomposition catalysts. In some embodiments, the compounds include porphyrin complexes containing substituted pyridine and/or imidazole substituents.

The invention is based in part on the discovery that substituted pyridyl- and substituted imidazolyl-porphyrins are unexpectedly effective peroxynitrite decomposition catalysts. Substituents on compounds as described herein can result in increased biocompatibility, which can be characterized as producing at least one of the following effects: (1) enhancement of the ONOO⁻ decomposition activity of the complex; (2) enhanced stability and half-life in vivo; (3) optimized tissue distribution throughout the body; and (4) lowered toxicity when administered to a subject. In some embodiments, the substituted compounds are present in liposomes.

Structures of Macrocyclic Compounds

Macrocyclic compounds include, e.g., substituted 3-(Formula I), 4-(Formula II), 2-(Formula IV) pyridylimidazoylyl porphyrins, and substituted (Formula III) imidazoylyl-porphyrins, where M, $L_1$ and $L_2$ are absent. Metal complexes with the substituted macrocyclic compounds according to the invention are shown below, where M is a metal and is preferably Mn or Fe:

Formula I

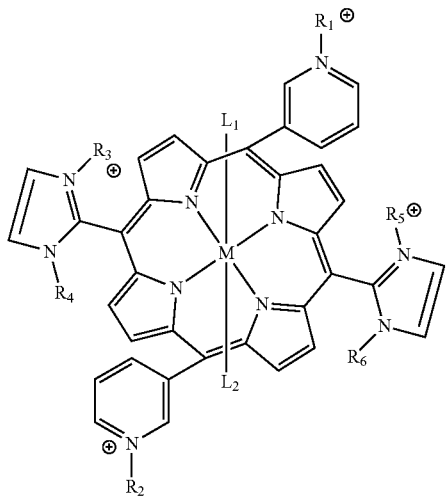

Formula II

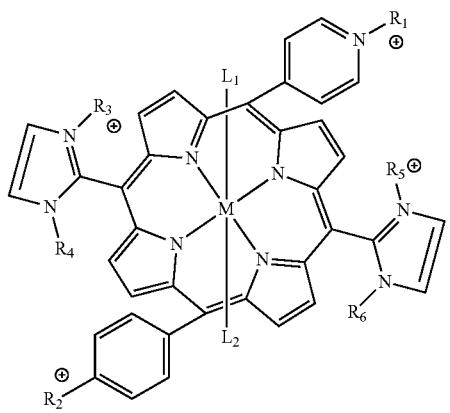

Formula III

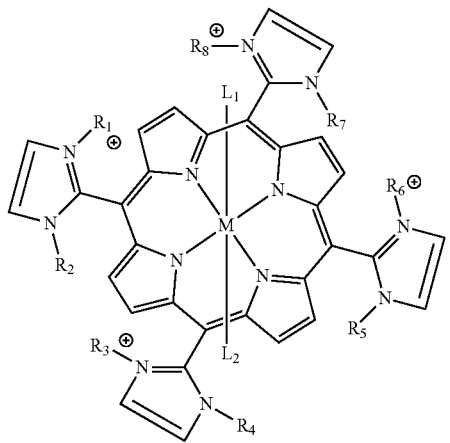

Formula IV

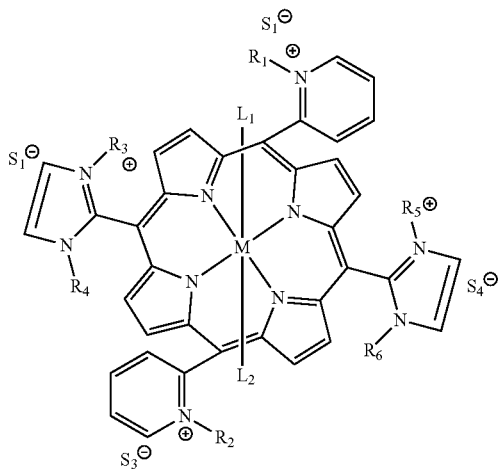

The invention also includes equivalents of the general formulae set forth above for the compounds, as well as the intermediates of the compounds that have the same general properties as these compounds. Also included are analogs of the compounds, e.g., compounds wherein one or more of the various R groups are simple variations of the substituents as defined therein, or substituents which are a higher alkyl group than that indicated.

Accordingly, in one aspect the invention provides a novel substituted porphyrin compound falling within formulae I, II, III, or IV as set forth in the Detailed Description of the Invention below.

$R_1$, $R_2$, $R_3$, $R_4$, $R_5$, $R_6$, and $R_7$ and $R_8$, when present, include, independently, those one or more linear, dendritic or branched polyethers, such as polyalkylene glycols (e.g., polyethylene glycol (PEG) moieties); linear, dendritic or branched polycarboxylic acids; oligosaccharides; peptides; steroids; and amino acids.

A "dendritic polymer" is a polymer exhibiting regular dendritic branching i.e. branching like a tree. It can be formed by the sequential or generational addition of branched layers to or from a core. The term dendritic polymer encompasses "dendrimers", which include a core, at least one interior branched layer, and a surface branched layer (see, e.g., Petar er al., Pages 641-645 in: Chem. in Britain, (August 1994). A "dendron" is a species of dendrimer having branches emanating from a focal point which is or can be joined to a core, either directly or through a linking moiety to form a dendrimer. Many dendrimers comprise two or more dendrons joined to a common core. However, the term dendrimer is used broadly to encompass a single dendron.

Highly branched dendritic polymers are well known and are discussed in, e.g., "Polymeric Materials Encyclopedia," Vol. 5 (1996), J. C. Salamone, Ed., CRC Press, New York, pp. 3049-3053. Dendritic polymers have a non-linear architecture and are intrinsically globular in shape. Discrete, stepwise synthetic methods are used to prepare highly branched pure compounds, or dendrimers. As discussed by Hawker and Devonport in "Step-Growth Polymers for High-Performance Materials: New Synthetic Methods," Hedrick, J. L. and Labadie, J. W., Eds., Am. Chem. Soc., Washington, D.C., 1996, pp. 186-196, if the macromolecule has highly regular branching which follows a strict geometric pattern, it is a dendrimer. Dendrimers are typically monodisperse and are prepared in a multi-step approach with purifications at each stage.

The architecture of dendrimers is also discussed by Roovers and Comanita in "Advances in Polymer Science," Vol. 142 (1999), Roovers, J., Ed., Springer, New York, pp. 179-228. Dendrimers consist of a core molecule which defines the center of symmetry of the molecule, and branching layers. Tomalia, et al., in Angew. Chem. Int. Ed. Eng., 29 (1990), 138-175 disclose "starburst" dendrimers which consist of an initiator core and branching groups.

Dendritic polymers include, but are not limited to, symmetrical and unsymmetrical branching dendrimers, cascade molecules, arborols (dumbbell shaped molecules in which a hydrophobic spacer separates two hydrophilic end groups), dense star polymers (symmetric, with branch arms of equal length, as disclosed in U.S. Pat. No. 5,714,166), and the like.

In some embodiments, the compounds are hyperbranched. Hyperbranched compounds result if the branching is random and irregular and are therefore not monodisperse. As discussed by Malmstroem, et al., in Macromolecules, 28 (1995), 1698-1703, a hyperbranched material contains a mixture of linear and fully branched repeating units and has a degree of branching of less than unity. A preferred dendritic substance has a degree of branching of unity. Even though not formed by regular sequential addition of branched layers, hyperbranched polymers, e.g., hyperbranched polyols, may be equivalent to a dendritic polymer where the branching pattern exhibits a degree of regularity approaching that of a dendrimer.

Peptidic dendrimer- and branched-peptides are disclosed in, e.g., U.S. Pat. Nos. 6,379,679, 5,714,166 and 5,622,933.

Branched and hyperbranched polyetherimides are disclosed in, e.g., U.S. Pat. No. 6,287,552. Enzymes modified by dendrimers are disclosed in, e.g., U.S. Pat. No. 6,379,942.

In one embodiment, the compounds of the invention include at least one of the polyethers disclosed herein. The remaining $R_1$, $R_2$, $R_3$, $R_4$, $R_5$, or $R_6$, or $R_7$, or $R_8$, when to present, are hydrogen. For example, the compounds of Formulae I, II, and TV contain at least one such polyether moiety and the remaining $R_1$, $R_2$, $R_3$, $R_4$, $R_5$, or $R_6$ are hydrogen, such that if one non-hydrogen R moiety is present, the remaining five such moieties are hydrogen. Where two of such R moieties are non-hydrogen, the remaining four moieties are hydrogen, etc. The compounds of Formula In contain at least one of the R moieties described herein, and the remaining $R_2$, $R_3$, $R_4$, $R_5$, $R_6$, $R_7$, or $R_8$ is hydrogen. Thus, if one of $R_2$, $R_3$, $R_4$, $R_5$, $R_6$, $R_7$, or $R_8$ is non-hydrogen, the remaining seven R moieties are hydrogen; if two of $R_2$, $R_3$, $R_4$, $R_5$, $R_6$, $R_7$, or $R_8$ are non-hydrogen, the remaining six R moieties are hydrogen, etc.

Figure 1B:
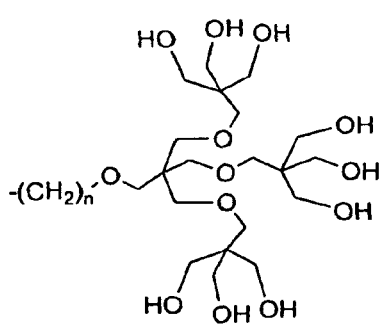
Figure 1B:
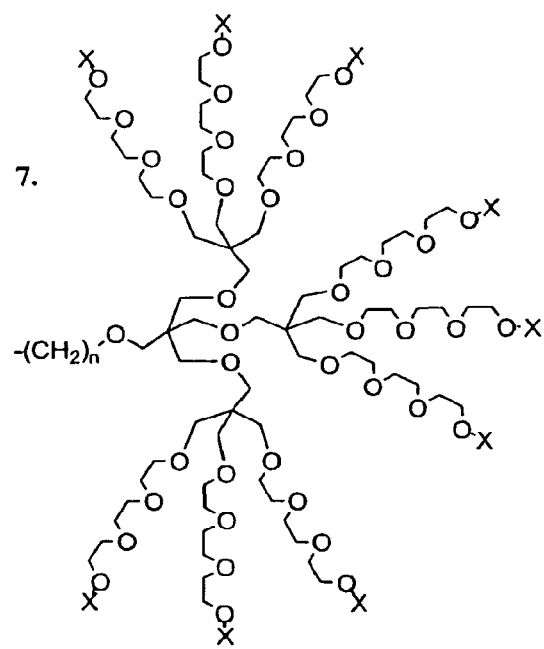

Examples of various R groups are shown in FIGS. 1A and 1B. Various substituent groups can vary in length according to the numbers of methylene ($CH_2$) or polyethylene glycol (PEG) groups included.

In one embodiment, one or more of $R_1$, $R_2$, $R_3$, $R_4$, $R_5$, $R_6$, $R_7$, or $R_8$ are $CH_2CH_2OCH_3$, $CH_2CH_2OCH_2CH_2OCH_3$ or $CH_2COO^-$.

In one embodiment, one or more of $R_1$, $R_2$, $R_3$, $R_4$, $R_5$, $R_6$, $R_7$, or $R_8$ is $(CH_2)_n-X$, where n is 1 to 10 and X is COOH; COOR'; $CONH_2$; CONHR'; $CONR'_2$; $CO(CH_2)_pR'$; $OPO_3H_2$; $PO_3H_2$; $SO_3H$; $NH_2$; $NR'_2$; or $NR'_3{}^+$. R' is alkyl, $CH_2CH_2OCH_3$, $CH_2CH_2OCH_2CH_2OCH_3$, $(CH_2)_n-X$, $(CH_2)_n-Y$, $(CH_2)_nAr-X$, $(CH_2)_nAr-Y$, $CH_2CH_2OCH_2CH_2OCH_2CH_2OCH_3$, $CH_2CO_2CH_2CH_3$, $(OCH_2CH_2)_m-X$, $(OCH_2CH_2)_m-Y$, $Y_2-X, Y_2C(Z_1)_3$, further wherein: $Z_1$ is $CH_2OCH_2(CH_2)_nX$ or $CH_2OCH_2(CH_2)_nY$; $(CH_2)_nC(O)Y_2C(Z_2)_3$, wherein: $Z_2$ is $CH_2OCH_2CH_2C(O)Y_2C(Z_4)_3$ and $Z_4$ is $CH_2OCH_2CH_2X$; $(CH_2)_nC(O)-Y_2-C(Z_5)_3$, wherein: $Z_5$ is $CH_2OCH_2CH_2C(O)Y_2C(Z_6)_3$ and $Z_6$ is $CH_2OCH_2CH_2C(O)O(CH_2CH_2O)_mCH_2CH_2O^-$; $(CH_2)_nOCH_2C(CH_2OH)_3$, $(CH_2)_nOCH_2CH(CH_2OH)_2$, $(CH_2)_nOCH_2C(CH_2OH)_2(CH_3)$, $(CH_2)_nOCH_2C[CH_2OCH_2C(CH_2OH)_3]_3$, $(CH_2)_nOCH_2C[CH_2OCH_2C(CH_2O[CH_2CH_2O]_mCH_2CH_2OX)_3]_3$, $CH_2CONH-Y$, $CH_2CO-Y$, and $CH_2CO(CH_2)_p-Y$, p is 1 or 2. In other embodiments, X is a steroid or amino acid. In still other embodiments, X is an oligosaccharide, a peptide, or a polycarboxylic acid.

In one embodiment, one or more of $R_1$, $R_2$, $R_3$, $R_4$, $R_5$, $R_6$, $R_7$, or $R_8$ is $(CH_2)_nAr-X$ or $(CH_2)_nAr-Y$, where Ar is substituted or unsubstituted phenyl or substituted or unsubstituted naphthyl, m is 1 to 200, and X is COOH; COOR'; $CONH_2$; CONHR'; $CONR'_2$; $CO(CH_2)_pR'$, $OPO_3H_2$; $PO_3H_2$; $-SO_3H$; $-NH_2$; $-NR_2$; or $-NR'_3{}^+$, where R' is alkyl, $CH_2CH_2OCH_3$, $CH_2CH_2OCH_2CH_2OCH_3$, $(CH_2)_n-X$, $(CH_2)_n-Y$, $(CH_2)_nAr-X$, $(CH_2)_nAr-Y$, $CH_2CH_2OCH_2CH_2OCH_2CH_2OCH_3$, $CH_2CO_2CH_2CH_3$, $(OCH_2CH_2)_m-X$, $(OCH_2CH_2)_m-Y$, $Y_2-X, Y_2C(Z_1)_3$, further wherein: $Z_1$ is $CH_2OCH_2(CH_2)_nX$ or $CH_2OCH_2(CH_2)_nY$; $(CH_2)_nC(O)Y_2C(Z_2)_3$, wherein: $Z_2$ is $CH_2OCH_2CH_2C(O)Y_2C(Z_4)_3$ and $Z_4$ is $CH_2OCH_2CH_2X$; $(CH_2)_nC(O)-Y_2-C(Z_4)_3$, wherein: $Z_5$ is $CH_2OCH_2CH_2C(O)Y_2C(Z_6)_3$ and $Z_6$ is $CH_2OCH_2CH_2C(O)O(CH_2CH_2O)_mCH_2CH_2O^-$; $(CH_2)_nOCH_2C(CH_2OH)_3$, $(CH_2)_nOCH_2CH(CH_2OH)_2$, $(CH_2)_nOCH_2C(CH_2OH)_2(CH_3)$, $(CH_2)_nOCH_2C[CH_2OCH_2C(CH_2OH)_3]_3$, $(CH_2)_nOCH_2C[CH_2OCH_2C(CH_2O[CH_2CH_2O]_mCH_2CH_2OX)_3]_3$, $CH_2CONH-Y$, $CH_2CO-Y$, and $CH_2CO(CH_2)_p-Y$, p is 1 or 2. In other embodiments, X is a steroid or amino acid. In still other embodiments, X is an oligosaccharide, a peptide, or a polycarboxylic acid. Y is OH or $(O-CH_2CH_2)_m-W_1$ or $(CH_2CH_2)_m-W_2$; where $W_1$ is OH, or $(O-(CH_2CH_2)_mOH)$ and $W_2$ is OR", further wherein R" is alkyl.

In one embodiment one or more of $R_1$, $R_2$, $R_3$, $R_4$, $R_5$, $R_6$, $R_7$, or $R_8$ is $(CH_2)-Y$, where n is 1 to 10 and Y is OH or $(O-CH_2CH_2)_m-W_1$ or $(CH_2CH_2)_m-W_2$; where $W_1$ is OH, or $(O-(CH_2CH_2)_mOH)$ and $W_2$ is OR", further wherein R" is alkyl.

In one embodiment one or more of $R_1$, $R_2$, $R_3$, $R_4$, $R_5$, $R_6$, $R_7$, or $R_8$ is $CH_2CONH-Y$, $CH_2COO-Y$, or $CH_2CO$ $(CH_2)_p-Y$, where p is 1 or 2 and Y is OH or $(O-CH_2CH_2)_m-W_1$ or $(CH_2CH_2)_m-W_2$; where $W_1$ is OH, or $(O-(CH_2CH_2)_mOH)$ and $W_2$ is OR", further wherein R" is alkyl.

In one embodiment, one or more of $R_1$, $R_2$, $R_3$, $R_4$, $R_5$, $R_6$, $R_7$, or $R_8$ is $(OCH_2CH_2)_m-Y$, where Y is OH or $(O-CH_2CH_2)_m-W_1$ or $(CH_2CH_2)_m-W_2$; where $W_1$ is OH, or $(OCH_2CH_2)_mOH$ and $W_2$ is OR", further wherein R" is alkyl and m is 1 to 200. In one embodiment, one or more of $R_1$, $R_2$, $R_3$, $R_4$, $R_5$, $R_6$, $R_7$, or $R_8$ is $(OCH_2CH_2)_m-X$, where m is 1 to 200, and X is COOH; COOR'; CONH$_2$; CONHR'; CONR'$_2$; CO(CH$_2$)$_p$R', OPO$_3$H$_2$; PO$_3$H$_2$; —SO$_3$H; —NH$_2$; —NR$_2$; or —NR'$_3^+$. R' is alkyl, $CH_2CH_2OCH_3$, $CH_2CH_2OCH_2CH_2OCH_3$, $(CH_2)-X$, $(CH_2)_n-Y$, $(CH_2)_nAr-X$, $(CH_2)_nAr-Y$, $CH_2CH_2OCH_2CH_2OCH_2CH_2OCH_3$, $CH_2CO_2CH_2CH_3$, $(OCH_2CH_2)_m-X$, $(OCH_2CH_2)_m-Y$, $Y_2-X$, $Y_2C(Z_1)_3$, further wherein: $Z_1$ is $CH_2OCH_2(CH_2)_nX$ or $CH_2OCH_2(CH_2)_nY$; $(CH_2)_nC(O)Y_2C(Z_2)_3$, wherein: $Z_2$ is $CH_2OCH_2CH_2C(O)Y_2C(Z_4)_3$ and $Z_4$ is $CH_2OCH_2CH_2X$; $(CH_2)_nC(O)-Y_2-C(Z_3)_3$, wherein: $Z_5$ is $CH_2OCH_2CH_2C(O)Y_2C(Z_6)_3$ and $Z_2$ is $CH_2OCH_2CH_2C(O)O(CH_2CH_2O)_mCH_2CH_2O^-$; $(CH_2)_nOCH_2C(CH_2OH)_3$, $(CH_2)_nOCH_2CH(CH_2OH)_2$, $(CH_2)_nOCH_2C(CH_2OH)_2(CH_3)$, $(CH_2)_nOCH_2C[CH_2OCH_2C(CH_2OH)_3]_3$, $(CH_2)_nOCH_2C[CH_2OCH_2C(CH_2O[CH_2CH_2O]_mCH_2CH_2OX)_3]_3$, $CH_2CONH-Y$, $CH_2CO-Y$, and $CH_2CO(CH_2)_p-Y$, p is 1 or 2. In other embodiments, X is a steroid or amino acid. In still other embodiments, X is an oligosaccharide, a peptide, or a polycarboxylic acid.

In one embodiment, one or more of $R_1$, $R_2$, $R_3$, $R_4$, $R_5$, $R_6$, $R_7$, or $R_8$ is $(OCH_2CH_2)_m-Y$, where m is 1 to 200, and Y is OH or $(O-CH_2CH_2)_m-W_1$ or $(CH_2CH_2)_m-W_2$; where $W_1$ is OH, or $(OCH_2CH_2)_mOH$ and $W_2$ is OR", further wherein R" is alkyl.

In one embodiment, one or more of $R_1$, $R_2$, $R_3$, $R_4$, $R_5$, $R_6$, $R_7$, or $R_8$ is $Y_2-X$, where $Y_2$ is $-(CH_2)_nO-$; $-(CH_2)_nNH-$; or $-(CH_2)_nS-$; $CH_2CONH-$, $CH_2COO-$, or $CH_2CO(CH_2)_p-$; where p is 1 or 2; n is 1 to 10, and X is —COOH; —COOR'; —CONH$_2$; —CONR'; —CONR'$_2$; CO(CH$_2$)$_p$R'; —OPO$_3$H$_2$; —PO$_3$H$_2$; —SO$_3$H —NH$_2$; —NR$_2$; or —NR'$_3^+$. R' is alkyl, $CH_2CH_2OCH_3$, $CH_2CH_2OCH_2CH_2OCH_3$, $(CH_2)-X$, $(CH_2)_n-Y$, $(CH_2)_nAr-X$, $(CH_2)_nAr-Y$, $CH_2CH_2OCH_2CH_2OCH_2CH_2OCH_3$, $CH_2CO_2CH_2CH_3$, $(OCH_2CH_2)_m-X$, $(OCH_2CH_2)_m-Y$, $Y_2-X$, $Y_2C(Z_1)_3$, further wherein: $Z_1$ is $CH_2OCH_2(CH_2)_nX$ or $CH_2OCH_2(CH_2)_nY$; $(CH_2)_nC(O)Y_2C(Z_2)_3$, wherein: $Z_2$ is $CH_2OCH_2CH_2C(O)Y_2C(Z_4)_3$ and $Z_4$ is $CH_2OCH_2CH_2X$; $(CH_2)_nC(O)-Y_2-C(Z_5)_3$, wherein: $Z_5$ is $CH_2OCH_2CH_2C(O)Y_2C(Z_5)_3$ and $Z_6$ is $CH_2OCH_2CH_2C(O)O(CH_2CH_2O)_mCH_2CH_2O^-$; $(CH_2)_nOCH_2C(CH_2OH)_3$, $(CH_2)_nOCH_2CH(CH_2OH)_2$, $(CH_2)_nOCH_2C(CH_2OH)_2(CH_3)$, $(CH_2)_nOCH_2C[CH_2OCH_2C(CH_2OH)_3]_3$, $(CH_2)_nOCH_2C[CH_2OCH_2C(CH_2O[CH_2CH_2O]_3, CH_2CH_2OX)_3]_3$, $CH_2CONH-Y$, $CH_2CO-Y$, and $CH_2CO$ $(CH_2)_p-Y$, p is 1 or 2. In other embodiments, X is a steroid or amino acid. In still other embodiments, X is an oligosaccharide, a peptide, or a polycarboxylic acid.

In one embodiment, one or more of $R_1$, $R_2$, $R_3$, $R_4$, $R_5$, $R_6$, $R_7$, or $R_8$ is $-CH_2CH_2OCH_2CH_2OCH_2CH_2OCH_3$ or $-CH_2CO_2CH_2CH_3$.

In one embodiment, one or more of $R_1$, $R_2$, $R_3$, $R_4$, $R_5$; $R_6$, $R_7$, or $R_8$ is $(CH_2)_nCH_2C(CH_2OH)_3$, and n=1 to 10, as shown in FIG. 1A, structure 4.

In one embodiment, one or more of $R_1$, $R_2$, $R_3$, $R_4$, $R_5$, $R_6$, $R_7$, or $R_8$ is $(CH_2)_nOCH_2C(CH_2OH)_2CH_3$ or $(CH_2)_nOCH_2CH(CH_2OH)_2$ and n=1 to 10, as shown in the structures represented in FIG. 1A (structure 5).

In one embodiment, one or more of $R_1$, $R_2$, $R_3$, $R_4$, $R_5$, $R_6$, $R_7$, or $R_8$ is $-Y_2C(Z_1)_3$, as shown in FIG. 1A, structure 1, where $Z_1$ is $CH_2OCH_2(CH_2)_n-X$ or $CH_2OCH_2(CH_2)_n-Y$, where $Y_2$ is $(CH_2)_nO$, $(CH_2)_nNH$, $(CH_2)_nS$, $CH_2CONH$, $CH_2COO$, or $CH_2CO(CH_2)_p$, where p is 1 or 2 and n is 1 to 10.

In one embodiment, one or more of $R_1$, $R_2$, $R_3$, $R_4$, $R_5$, $R_6$, $R_7$, or $R_8$ is $(CH_2)_nC(O)Y_2C(Z_2)_3$, where $Z_2$ is $CH_2OCH_2CH_2C(O)Y_2C(Z_4)_3$, where $Z_4$ is $CH_2OCH_2CH_2X$, in the compound shown in FIG. 1B, structure 2, X is COOH.

In one embodiment, one or more of $R_1$, $R_2$, $R_3$, $R_4$, $R_5$, $R_6$, $R_7$, or $R_8$ is $(CH_2)_nC(O)-Y_2-C(Z_5)_3$, where $Z_5$ is $CH_2OCH_2CH_2C(O)Y_2C(Z_6)_3$, where 4 is $CH_2OCH_2CH_2C(O)O(CH_2CH_2O)_mCH_2CH_2O$, as shown in FIG. 1A, structure 3. In one embodiment, structure 3 is complexed with any suitable charge neutralizing cation, to form a salt.

In one embodiment, one or more of $R_1$, $R_2$, $R_3$, $R_4$, $R_5$, $R_6$, $R_7$, or $R_8$ is $-(CH_2)_nOCH_2C[CH_2OCH_2C(CH_2OH)_3]_3$ as shown in FIG. 1B, structure 6; or $-(CH_2)_nOCH_2C[CH_2OCH_2C(CH_2O[CH_2CH_2O]_mCH_2CH_2OX)_3]_3$, as shown in FIG. 1B, structure 7 where n is 1-10 and m is 1-200, and X is as defined above.

In one embodiment, one or more of $R_1$, $R_2$, $R_3$, $R_4$, $R_5$, $R_6$, $R_7$, or $R_8$ is a $-(CH_2)_nNHCO$ motif, a $-(CH_2)_nCONH$ motif, a $(CH_2)_nCOO$ motif, or a $(CH_2)_nCO(CH_2)_p$ motif where n=1 to 10, p is 1 or 2, and the motif can be linked to a polyalkylene glycol (e.g., polyethylene glycol) polymer, an amino acid, a peptide, or a polypeptide an oligosaccharide, a polycarboxylic acid, or a steroid. In one embodiment, when the compound is Formula III, then $R_1$, $R_2$, $R_3$, $R_4$, $R_5$, $R_6$, $R_7$, or $R_8$ when present are not all $CH_2CH_2OCH_3$. In another embodiment, when the compound is Formula III, then Ar is not an unsubstituted phenyl when n is 1 and X is COOH.

In one embodiment, M is absent or a metal. In another embodiment, M is Mn, Fe, or Zn. In another embodiment, M is M or Fe.

In one embodiment, the compounds are provided in association with suitable ligands ($L_1$ and $L_2$) and/or charge neutralizing anions. $L_1$ and $L_2$ can be the same or different, and one or more may be absent. Ligands and charge neutralizing anions can be derived from any monodentate or polydentate coordinating ligand or ligand system or the corresponding anion thereof. They are independently selected from the group consisting of halide, oxo, aquo, hydroxo, alcohol, phenol, dioxygen, peroxo, hydroperoxo, alkylperoxo, arylperoxo, ammonia, alkylamino, arylamino, heterocycloalkyl amino, heterocycloaryl, amino, amine oxides, hydrazine, alkyl hydrazine, aryl hydrazine, nitric oxide, cyanide, cyanate, thiocyanate, isocyanate, isothiocyanate, alkyl nitrile, aryl nitrile, alkyl isonitrile, aryl isozutrile, nitrate, nitrite, azido, alkyl sulfonic acid, aryl sulfonic acid, alkyl sulfoxide, aryl sulfoxide, alkyl aryl sulfoxide, alkyl sulfenic acid, aryl sulfenic acid, alkyl sulfinic acid, aryl sulfinic acid, alkyl thiol carboxylic acid, aryl thiol carboxylic acid, alkyl thiol thiocarboxylic acid, aryl thiol thiocarboxylic acid, alkyl carboxylic acid, aryl carboxylic acid, urea, alkyl urea, aryl urea, alkyl aryl urea, thiourea, alkyl thiourea, aryl thiourea, alkyl aryl thiourea, sulfate, sulfite, bisulfate, bisulfite, thiosulfate, thiosulfite, hydrosulfite, alkyl phosphine, aryl phosphine, alkyl phosphine oxide, aryl phosphine oxide, alkyl aryl phosphine oxide, alkyl phosphine sulfide, aryl phosphine sulfide, alkyl aryl phosphine sulfide, alkyl phosphonic acid, aryl phosphonic acid, alkyl phosphinic acid, aryl phosphinic acid, alkyl phosphinous acid, aryl phosphinous acid, phosphate, thiophosphate, phosphite, pyrophosphite, triphosphate, hydrogen phosphate, dihydrogen phosphate, alkyl guanidino, aryl guanidino, alkyl aryl guanidino, alkyl carbamate, aryl carbamate, alkyl aryl carbamate, alkyl thiocarbamate, aryl thiocarbamate, alkyl aryl thiocarbamate, alkyl ditbiocarbamate, aryl dithiocarbamate, alkyl aryl dithiocarbamate, bicarbonate, carbonate, perchlorate, chlorate, chlorite, hypochlorite, perbromate, bromate, bromite, hypobromite, tetrahalomanganate, tetrafluoroborate, hexafluorophosphate, hexafluoroanitmonate, hypophosphite, iodate, periodate, metaborate, tetraaryl borate, tetra alkyl borate, tartrate, salicylate, succinate, citrate, ascorbate, saccharinate, amino acid, hydroxamic acid, thiotosylate, and anions of ion exchange resins, or systems; with the proviso that when the charge neutralizing complex has a net positive charge, then D is a negatively charged counter ion or when the charge neutralizing complex has net negative charge then D is a counter ion selected from a group consisting of alkaline and alkaline earth cations, organic cations such as alkyl or alkylaryl ammonium cations.

Preferred ligands include halide, oxo, aquo, hydroxo and alcohol. Preferred anionic counterions include halide ions. Halide ions include fluoro, chloro, bromo or iodo ions. Ligands and counterions may be the same or different. For example, a metallic complex may have one or two chloro axial ligands and 1, 2, 3, or 4 chloride ions as charge neutralizing anions.

As utilized herein, the term "alkyl", alone or in combination, means a straight-chain or branched-chain alkyl radical containing from 1 to about 22 carbon atoms, preferably from about 1 to about 18 carbon atoms, and most preferably from about 1 to about 12 carbon atoms. Examples of such radicals include, but are not limited to methyl, ethyl, n-propyl, isopropyl, n-butyl, isobutyl, sec-butyl, tert-butyl, pentyl, iso-amyl, hexyl, octyl, nonyl, decyl, dodecyl, tetradecyl, hexadecyl, octadecyl and eicosyl. Lower alkyl refers to a straight-chain or branched-chain alkyl radical containing from 1 to 6 carbon atoms.

The term "aryl" or "Ar", alone or in combination, means a phenyl or naphthyl radical which optionally carries one or more substituents selected from alkyl, cycloalkyl, cycloalkenyl, aryl, heterocycle, alkoxyaryl, alkaryl, alkoxy, halogen, hydroxy, amine, cyano, nitro, alkylthio, phenoxy, ether, trifluoromethyl and the like, such as phenyl, p-tolyl, 4-methoxyphenyl, 4-(tert-butoxy)phenyl, 4-fluorophenyl, 4-chlorophenyl, 4-hydroxyphenyl, 1-naphthyl, 2-naphthyl, and the like.

The term "aralkyl", alone or in combination, means an alkyl or cycloalkyl radical as defined herein in which one hydrogen atom is replaced by an aryl radical as defined herein, such as benzyl, 2-phenylethyl, and the like.

The term "heterocyclic" means ring structures containing at least one other kind of atom, in addition to carbon, in the ring. The most common of the other kinds of atoms include nitrogen, oxygen and sulfur. Examples of heterocycles include, but are not limited to, pyrrolidinyl, piperidyl, imidazolidinyl, tetrahydrofuryl, tetrahydrothienyl, furyl, thienyl, pyridyl, quinolyl, isoquinolyl, pyridazinyl, pyrazinyl, indolyl, imidazolyl, oxazolyl, thiazolyl, pyrazolyl, pyridinyl, benzoxadiazolyl, benzothiadiazolyl, triazolyl and tetrazolyl groups.

The term "cycloalkyl", alone or in combination means a cycloalkyl radical containing from 3 to about 10, preferably from 3 to about 8, and most preferably from 3 to about 6 carbon atoms. Examples of such cycloalkyl radicals include, but are not limited to, cyclopropyl, cyclobutyl, cyclopentyl, cyclohexyl, cycloheptyl, cyclooctyl, and perhydronaphthyl.

The term "cycloalkenyl", alone or in combination, means a cycloalkyl radical having one or more double bonds. Examples include, but are not limited to, cyclopentenyl, cyclohexenyl, cyclooctenyl, cyclopentadienyl, and cyclooctadienyl.

The term "metal(s)" refers to any atom of the Periodic Table having the properties of a metal. These include preferably all transition metals, actinides and lanthanides. More preferably tin, silicon, germanium, copper, iron, cobalt, zinc, nickel or manganese are used. See *Porphyrins and Metalloporphyrins* by K. M. Smith, Elsevier/North-Holland Biochemical Press (1976), which is incorporated herein in its entirety by reference. "Metal salt" refers to an organic or inorganic salt used to treat a dihydro-porphyrin compound to produce the corresponding metal porphyrin compound. Acetates and propionates are preferred.

The term "pharmacologically effective amount" as used herein means an amount that slows or prevents the progression of the targeted disease or pathology. It is preferable that the slowing or prevention not be accompanied by a toxic effect that offsets the medical value of slowing or preventing the progression of the targeted disease or pathology.

The "pharmaceutically acceptable carrier" must be "acceptable" in the sense of being compatible with the compounds or compositions of the invention and not deleterious to the subject to be treated. Preferably, the carrier is also capable of stabilizing the compound or composition.

Salts encompassed within the term "pharmaceutically acceptable salts" refer to non-toxic salts of the compounds of this invention which are generally prepared by reacting the free base with a suitable organic or inorganic acid to produce "pharmaceutically-acceptable acid addition salts" of the compounds described herein. In another embodiment, the free acid is reacted with a suitable organic or inorganic base to produce "pharmaceutically-acceptable base addition salts" of the compounds described herein. These compounds retain the biological effectiveness and properties of the free acids and free bases. Representative of such salts are the water-soluble and water-insoluble salts, such as the acetate, amsonate (4,4-diaminostilbene-2,2'-disulfonate), benzenesulfonate, benzonate, bicarbonate, bisulfate, bitartrate, borate, bromide, butyrate, calcium edetate, camsylate, carbonate, chloride, citrate, clavulariate, dihydrochloride, edetate, edisylate, estolate, esylate, fumarate, gluceptate, gluconate, glutamate, glycollylarsanilate, hexafluorophosphate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, 3-hydroxy-2-naphthoate, oleate, oxalate, palmitate, pamoate (1,1-methylene-bis-2-hydroxy-3-naphthoate, embonate), pantothenate, phosphate/diphosphate, picrate, polygalacturonate, propionate, p-toluenesulfonate, salicylate, stearate, subacetate, succinate, sulfate, sulfosaliculate, suramate, tannate, tartrate, teoclate, tosylate, triethiodide, and valerate salts.

In one embodiment, the compound is based on a porphyrin structure. As used herein, the term "porphyrin" includes compounds prior to a metal atom being inserted into the ring system, as well as molecular systems in which compounds are attached to the metal. The substituents, as well as the overall porphyrin structure, can be neutral, positively charged, or negatively charged.

Synthesis of Peroxynitrite Decomposition Catalysts

In various embodiments, the macrocyclic compounds of the invention are provided as a metallic complex. The metallic complexes can be, e.g., porphyrin-iron or porphyrin-manganese complexes.

Starting porphyrins can be prepared according to methods well known in the art. The methods can include, for example, those described in WO95/31197, Campestrini and Meunier, Inorg. Chem. 31, 1999-2006, (1992); Robert et al., Inorg. Chem. 30, 706-711, (1991); Lindsey and Wagner, J. Org. Chem. 54, 828-836, (1989); and Zipplies, et al., J. Am. Chem. Soc. 108, 4433-4445, (1986). See, also, Meltze; Phthalocyanine Technology in Chemical Process Reviews No. 42; Noyes Data Corp. Park Ridge, N.J. (1970). See, also, Goedken, et al., J.C.S. Chem. Comm. 337-338, (1973); Martin, and Cummings, Inorg. Chem. 12, 1477-1482, (1973); Riley, et al., J. Am. Chem. Soc. 98, 1752-1762, (1976); Dabrowiak, et al., J. Am. Chem. Soc. 95, 6613-6622, (1973); Riley and Busch, Inorg. Chem. 23, 3235-3241, (1984); Watkuns, et al., Inorg. Chem. 15, 387-393, (1976); and Riley, et al., J. Am. Chem. Soc. 99, 767-777, (1977). Pyridinium porphyrins can also be synthesized as described in Hunt et al., in Chem. & Biol. 4:845-58, 1997. Substituted porphyrins can also be synthesized as described herein.

Where a substituent is designated as, or can be, a hydrogen, the exact chemical nature of a substituent which is other than hydrogen at that position, e.g., a hydrocarbyl radical or a halogen, hydroxy, amino and the like functional group, is not critical so long as it does not adversely affect the overall activity and/or synthesis procedure. Where a ligand ($L_1$ and $L_2$) or a charge neutralizing anion is designated as a particular chemical entity, the exact chemical nature of a ligand or a charge neutralizing anion which is other than the particular chemical entity depicted is not critical so long as it does not adversely affect the overall activity and/or synthesis procedure.

Properties of the imidazolyl-compounds of the invention can be determined using methods known in the art. For example, methods for determining pKa, electronic absorption spectra, phosphate binding, cyanide binding, EPR spectroscopy in the presence of increasing KCN concentrations, magnetic susceptibility, ascorbate reduction, and electrochemical reduction are described in methods for electronic spectral, magnetic and electrochemical properties of imidazolyl-containing compounds as described in D. E. Lahaye, *Water-Soluble meso Imidazolyl Manganese Porphyrins: Biomimetics and Oxidation Catalysis*, Doctoral Dissertation, Princeton University, 2005.

Synthesis of Amphiphilic Catalysts and Preparation of Vesicular Assembly Systems According to the Invention The invention includes amphiphilic compounds. In one embodiment, the amphiphic compound contains a metallic complex, e.g., a metallic porphyrin compound. Porphyrin compounds can be synthesized as described generally in Hunt et al., in Chem. & Biol. 4:845-58, 1997. Substituted metallic complex amphiphiles within the invention are prepared by methods known in the art. Polyether cascade dendritic porphyrins can be prepared resulting in a symmetrical solution dendrimer. If desired, unsymmetrical derivatives with a single hydrophobic side chain can be readily prepared by procedures known in the art. While not wishing to be bound by theory, it is believed the side chains of the invention ($R_1$, $R_2$, $R_3$, $R_4$, $R_5$, and $R_6$, and $R_7$, and $R_8$ when present) lower toxicity by minimizing or preventing liver uptake, thereby allowing the compound to be maintained longer in a subject's blood pool. If desired, targeting agents such as steroids can be attached.

Amphiphilic porphyrin compound analogs can include end products synthesized using procedures generally described Hunt et al., in Chem. & Biol 4:845-58, 1997. For example, iron and manganese porphyrins can be constructed by using as starting materials pyridium porphyrins that are synthesized according to methods known to those skilled in the art and referenced above. For example, pyridium porphyrins can be synthesized by peralkylation of 5,10,15,20,-tetrakis(4-pyridyl)porphine with an appropriate alkyl iodide, e.g., dodecyl iodide.

Porphyrins preferably are located in a hydrophilic environment for the efficient catalysis of peroxynitrite. Thus, in preferred embodiments, the invention includes PEG-linked (polyethylene glycol) substituted porphyrin compounds. In certain aspects of the invention, these porphyrins can be provided in vesicular assemblies, such as liposomes. In such an environment, the PEG-linkers extend the metalloporphyrin headgroup away from the interfacial region between the membrane and external solution and further into the bulk solvent. The hydrophilicity of the porphyrin headgroup correlates with the efficiency of the catalysts: the rate of peroxynitrite decomposition is much faster when catalyzed by PEG-linked metalloporphyrins, as compared to metalloporphyrins with simple dodecyl chains. In some embodiments, tocopherol, e.g., $\alpha$ tocopherol or, preferably, $\gamma$ tocopherol, is also present in the vesicular assembly.

The compounds can possess one or more asymmetric carbon atoms and are thus capable of existing in the form of optical isomers as well as in the form of racemic or nonracemic mixtures thereof. The optical isomers can be obtained by resolution of the racemic mixtures according to conventional processes, including by formation of diastereoisomeric salts through treatment with an optically active acid (e.g., tartaric, diacetyltartaric, dibenzoyltartaric, ditoluoyltartaric and camphorsulfonic) and then separation of the mixture of diastereoisomers by crystallization followed by liberation of the optically active bases from these salts. Another process for separation of optical isomers involves the use of a chiral chromatography column optimally chosen to maximize the separation of the enantiomers. Still another available method involves synthesis of covalent diastereoisomeric molecules by reacting one or more secondary amine group(s) of the compounds of the invention with an optically pure acid in an activated form or an optically pure isocyanate. The synthesized diastereoisomers can be separated by conventional means such as chromatography, distillation, crystallization or sublimation, and then hydrolyzed to deliver the enantiomerically pure ligand. The optically active compounds of the invention can likewise be obtained by utilizing optically active starting materials, such as natural amino acids.

The chemical reactions shown by the references described above are generally disclosed in terms of variations appropriate for their broadest application to the preparation of the compounds of this invention. Occasionally, the reactions may not be applicable as described to each compound included within the disclosed scope. The compounds for which this occurs will be readily recognized by those skilled in the art. In all such cases, either the reactions can be successfully performed by conventional modifications known to those skilled in the art, e.g., by appropriate protection of interfering groups, by changing to alternative conventional reagents, by routine modification of reaction conditions, or the like. Alternatively, other reactions disclosed herein or otherwise conventionally known, will be applicable to the preparation of the corresponding compounds of this invention. In all preparative methods, all starting materials are known or can be readily prepared from known starting materials.

Additional methods for synthesizing compounds according to the invention are described in the Examples, below.

Screening Compounds for Catalytic Activity

To screen compounds for peroxynitrite decomposition catalytic activity of the invention, peroxynitrite is prepared and isolated as its sodium salt by the reaction of acidic hydrogen peroxide with sodium nitrite followed by rapid quenching with NaOH as set out by Halfpenny and Robinson, in *J. Chem. Soc.*, 928-938 (1952). Peroxynitrite has an absorbance maximum at 302 nm with an extinction coefficient of 1670 $M^{-1}$ $cm^{-1}$. Therefore, it is possible to directly observe the decomposition of peroxynitrite by monitoring the change in absorbance at 302 nm by stop-flow spectrophotometric analysis. For example, the decomposition of peroxynitrite at an accelerated rate (relative to the natural decomposition rate of peroxynitrite) upon the addition of the decomposition catalysts of the invention.

In addition, it is known that peroxynitrite inactivates CuZn—SOD (superoxide dismutase) enzyme in a concentration dependant manner. Peroxynitrite is also reported to inactivate Mn—SOD. See Ischiropoulos et al., *Archives of Biochemistry and Biophysics*, 298:2, 431-437 (1992). The invention provides compounds and methods for screening for compounds which protect CuZn—SOD or Mn—SOD by inactivating peroxynitrite.

Peroxynitrite catalytic activity can also be measured using methods described in Hunt et al., Chem. & Biol. 4:845-58, 1997.

Pharmaceutical Compositions

The pharmaceutical compositions of the invention include a pharmaceutically effective amount of one or more of the compounds of the invention administered in a dosage regimen appropriate for treating a disease condition. The dosage regimen is selected in accordance with a variety, of factors, including the type, age, weight, sex, diet and medical condition of the patient, the severity of the disease, the route of administration, pharmacological considerations such as the activity, efficacy, pharmacokinetic and toxicology profiles of the particular compound employed, whether a drug delivery system is utilized and whether the compound is administered as part of a drug combination. Thus, the dosage regimen actually employed may vary widely and therefore may deviate from the preferred dosage regimen set forth above.

For example, total daily dose administered to a mammal in single or divided doses may be in amounts, for example, from about 1 to about 100 mg/kg body weight daily and more usually about 3 to 30 mg/kg. Dosage unit compositions may contain such amounts of submultiples thereof to make up the daily dose. The number of submultiples is preferably about one to three times per day of about 30 mg/kg per unit dosage form. The serum concentrations of the doses are about 1 µM to 1.5 µM, e.g., 3 pM-1.0 µM, 300 pM to 750 nM, 500 pM to 250 nM, or 1 nm to 125 nM. Furthermore, the amount of active ingredient that may be combined with the carrier materials to produce a single dosage form will vary depending upon the host treated and the particular mode of administration.

The invention also includes pharmaceutical compositions suitable for decomposing peroxynitrite in a cell both in vivo and in vitro. More preferably, the invention includes pharmaceutical compositions suitable for decompcising peroxynitrite under physiological conditions. The compositions are preferably suitable for internal use and include an effective amount of a pharmacologically active compound of the invention, alone or in combination, with one or more pharmaceutically acceptable carriers. The compounds are especially useful in that they have very low, if any toxicity.

In practice, the compounds of the inventions or their pharmaceutically acceptable salts, are administered in amounts which will be sufficient to inhibit inflammatory conditions or disease and/or prevent the development of inflammation or inflammatory disease in animals or mammals, and are used in the pharmaceutical form most suitable for such purposes.

Preferred pharmaceutical compositions are tablets and gelatin capsules comprising the active ingredient together with a) diluents, e.g., lactose, dextrose, sucrose, mannitol, sorbitol, cellulose and/or glycine; b) lubricants, e.g., silica, talcum, stearic acid, its magnesium or calcium salt and/or polyethyleneglycol; for tablets also c) binders, e.g., magnesium aluminum silicate, starch paste, gelatin, tragacanth, methylcellulose, sodium carboxymethylcellulose and/or polyvinylpyrrolidone; if desired d) disintegrants, e.g., starches, agar, alginic acid or its sodium salt, or effervescent mixtures; and/or e) absorbents, colorants, flavors and sweeteners. Injectable compositions are preferably aqueous isotonic solutions or suspensions, and suppositories are advantageously prepared from fatty emulsions or suspensions. The compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. The compositions are prepared according to conventional mixing, granulating or coating methods, respectively, and contain about 0.1 to 75%, preferably about 1 to 50%, of the active ingredient. Administration of the active metallic complexes of the inventions and salts described herein can be via any of the accepted modes of administration for therapeutic agents. These methods include systemic or local administration such as oral, nasal, parenteral, transdermal, subcutaneous, or topical administration modes.

Depending on the intended mode of administration, the compositions may be in solid, semi-solid or liquid dosage form, such as, for example, injectables, tablets, suppositories, pills, time-release capsules, powders, liquids, suspensions, or the like, preferably in unit dosages. The compositions will include an effective amount of active metallic complexes of the invention or the pharmaceutically acceptable salt thereof, and in addition, and may also include any conventional pharmaceutical excipients and other medicinal or pharmaceutical drugs or agents, carriers, adjuvants, diluents, etc., as are customarily used in the pharmaceutical sciences.

For solid compositions, excipients include pharmaceutical grades of mannitol, lactose, starch, magnesium stearate, sodium saccharin, talcum, cellulose, glucose, sucrose, magnesium carbonate, and the like may be used. The active metallic complexes of the invention may be also formulated as suppositories using for example, polyalkylene glycols, for example, propylene glycol, as the carrier.

Liquid, particularly injectable compositions can, for example, be prepared by dissolving, dispersing, etc. The active metallic complexes of the invention is dissolved in or mixed with a pharmaceutically pure solvent such as, for example, water, saline, aqueous dextrose, glycerol, ethanol, and the like, to thereby form the injectable solution or suspension.

If desired, the pharmaceutical composition to be administered may also contain minor amounts of non-toxic auxiliary substances such as wetting or emulsifying agents, pH buffering agents, and other substances such as for example, sodium acetate, triethanolamine oleate, etc.

Parental injectable administration is generally used for subcutaneous, intramuscular or intravenous injections and infusions. Injectables can be prepared in conventional forms, either as liquid solutions or suspensions or solid forms suitable for dissolving in liquid prior to injection. One approach for parenteral administration employs the implantation of a slow-release or sustained-released systems, which assures that a constant level of dosage is maintained, according to U.S. Pat. No. 3,710,795.

The compounds of the invention can be administered in such oral dosage forms as tablets, capsules (each including timed release and sustained release formulations), pills, powders, granules, elixirs, tinctures, suspensions, syrups and emulsions. Likewise, they to may also be administered in intravenous (both bolus and infusion), intraperitoneal, subcutaneous or intramuscular form, all using forms well known to those of ordinary skill in the pharmaceutical arts.

The dosage regimen utilizing the compounds is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician or veterinarian can readily determine and prescribe the effective amount of the drug required to prevent, counter or arrest the progress of the condition.

Oral dosages of the invention, when used for the indicated effects, will range between about 0.05 to 1000 mg/day orally. The compositions are preferably provided in the form of scored tablets containing 0.5, 1.0, 2.5, 5.0, 10.0, 15.0, 25.0, 50.0, 100.0, 250.0, 500.0 and 1000.0 mg of active ingredient. Effective plasma levels of the compounds of the invention range from 0.002 mg to 50 mg per kg of body weight per day.

Compounds of the invention may be administered in a single daily dose, or the total daily dosage may be administered in divided doses of two, three or four times daily. Furthermore, preferred metallic complexes for the invention can be administered in intranasal form via topical use of suitable intranasal vehicles, or via transdermal routes, using those forms of transdermal skin patches well known to those of ordinary skill in that art. To be administered in the form of a transdermal delivery system, the dosage administration will, of course, be continuous rather than intermittent throughout the dosage regimen. Other preferred topical preparations include creams, ointments, lotions, aerosol sprays and gels, wherein the concentration of active ingredient would range from 0.1% to 15%, w/w or w/v.

The compounds herein described in detail can form the active ingredient, and are typically administered in admixture with suitable pharmaceutical diluents, excipients or carriers (collectively referred to herein as "carrier" materials) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic pharmaceutically acceptable inert carrier such as ethanol, glycerol, water and the like. Moreover, when desired or necessary, suitable binders, lubricants, disintegrating agents and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

The compounds of the invention can also be administered in the form of liposome delivery systems, such as small unilamellar vesicles, large unilamellar vesicles and multilamellar vesicles. Liposomes can be formed from a variety of phospholipids, containing cholesterol, stearylamine or phosphatidylcholines. In some embodiments, a film of lipid components is hydrated with an aqueous solution of drug to a form lipid layer encapsulating the drug, as described in U.S. Pat. No. 5,262,564.

Compounds of the invention may also be delivered by the use of monoclonal antibodies as individual carriers to which the metallic complex molecules are coupled. The compounds of the invention may also be coupled with soluble polymers as targetable drug carriers. Such polymers can include polyvinylpyrrolidone, pyran copolymer, polyhydroxypropyl-methacrylamide-phenol, polyhydroxyethylaspanamidephenol, or polyethyleneoxidepolylysine substituted with palmitoyl residues. Furthermore, the metallic complexes of the invention may be coupled to a class of biodegradable polymers useful in achieving controlled release of a drug, for example, polylactic acid, polyepsilon caprolactone, polyhydroxy butyric acid, polyorthoesters, polyacetals, polydihydropyrans, polycyanoacrylates and cross-linked or amphipathic block copolymers of hydrogels. Any of the above pharmaceutical compositions may contain 0.1-99%, preferably 1-70% of the active metallic complexes, especially metallic complexes of the Formula I as active ingredients.

While the compounds of the invention can be administered as the sole active pharmaceutical agent, they can also be used in combination with one or more compounds of the invention or with one or more compounds which are known to be effective against the specific disease state that one is targeting for treatment.

Therapeutic Methods

The invention also provides methods for preventing or reducing cellular damage to resulting from exposure to various chemical compounds which produce potentially damaging free radical species, comprising administering a therapeutically or prophylactically efficacious dosage of at least one species of a substituted compound of the invention, e.g., a substituted metalloporphyrin.

Compositions including the herein described compounds may be administered for various indications, including: (1) for preventing ischemic reoxygenation injury in a patient, (2) for preserving organs for transplant in an anoxic, hypoxic, or hyperoxic state prior to transplant, (3) for protecting normal tissues from free radical-induced damage consequent to exposure to ionizing radiation and/or chemotherapy, as with bleomycin, (4) for protecting cells and tissues from free radical-induced injury consequent to exposure to xenobiotic compounds which form free radicals, either directly or as a consequence of monooxygenation through the cytochrome P-450 system, (5) for enhancing cryopreservation of cells, tissues, organs, and organisms by increasing viability of recovered specimens, and (6) for prophylactic administration to prevent: carcinogenesis, cellular senescence, cataract formation, formation of malondialdehyde adducts, HIV pathology and macromolecular crosslinking, such as collagen crosslinking. In one aspect of the invention, compound-metal complexes (e.g., metalloporphyrins) are formulated for administration by the oral route by forming a pharmaceutical dosage form comprising an excipient and not less than 1 microgram nor more than about 10 grams of at least one antioxidant complex of the invention. Dietary formulations are administered for therapy of free radical-induced diseases and/or for the chemoprevention of neoplasia and/or oxidative damage associated with normal aerobic metabolism.

In another aspect, buffered aqueous solutions comprising one or more antioxidant substituted compounds of the invention, e.g., a substituted metalloporphyrin, at a concentration of at least 1 nM but not more than about 100 mM is formulated for administration, usually at a concentration of about 0.1 to 10 mM, to a patient undergoing or expected to undergo: (1) an ischemic episode, such as a myocardial infarction, cerebral ischemic event, transplantation operation, open heart surgery, elective angioplasty, coronary artery bypass surgery, brain surgery, renal infarction, traumatic hemorrhage, tourniquet application, (2) antineoplastic or antihelminthic chemotherapy employing a chemotherapeutic agent which generates free radicals, (3) endotoxic shock or sepsis, (4) exposure to ionizing radiation, (5) exposure to exogenous chemical compounds which are free radicals or produce free radicals, (6) thermal or chemical burns or ulcerations, (7) hyperbaric oxygen, or (8) apoptosis of a predetermined cell population (e.g., lymphocyte apoptosis). Administration can be via any desired route, e.g., intravenous, subcutaneous, inhalation, intramuscular. The buffered aqueous solutions may also be used, typically in conjunction with other established methods, for organ culture, cell culture, transplant organ maintenance, and myocardial irrigation. Non-aqueous formulations, such as lipid-based formulations are also provided, including stabilized emulsions. The invention also encompasses pharmaceutical compositions of compound-metal complexes, therapeutic uses of such complexes, methods and compositions for using these complexes in diagnostic, therapeutic, and research applications in human and veterinary medicine.

Another aspect of the invention is its use in enhancing the recovery of skin of a warm-blooded animal from wounds, such as surgical incisions, burns, inflammation or minor irritation due to oxidative damage, etc. This method includes administering to the skin wound or irritation a therapeutically or, in some cases a prophylactically effective amount of a composition which comprises a substituted compound, e.g. a substituted metalloporphyrin, as described herein. Additionally, the invention provides a method of treating a peroxide-induced condition in a subject which comprises administering to the subject an amount of any of the compounds of the invention effective to reduce peroxide in a subject and thereby treat the peroxide-induced condition. Administration of the compound to the subject may be effected by means other than those listed herein. Further, the peroxide-induced condition may involve cataracts, inflammation of a tissue, ischemia, an allergic reaction, or pathology caused by oxidative stress. Where the peroxide-induced condition involves cataracts, administration is effected by, but is not limited to, topical contact to the surface of an eye.

The method includes contacting the cell with any compound of formulae I, II, III, or IV in a pharmaceutically effective amount, that is, sufficient to actively decompose peroxynitrite in the cell. In general, any cell having peroxynitrite, or capable of synthesizing peroxynitrite, can be treated. The cell can be provided in any form so long as it is accessible to the compound. For example, the cell can be provided in vitro, ex vivo, or in vivo. Peroxynitrite decomposition can be measured using any method known in the art, e.g., methods such as stopped-flow kinetic analysis.

Also provided in the invention is a method of inhibiting, preventing, or treating a pathology advantageous affected by the decomposition of peroxynitrite in a mammal. The disease or pathology can be associated, e.g., with an inflammatory disease or neurodegenerative disease characterized by the presence of peroxynitrite. Inflammatory to diseases refer to diseases or conditions where there is an inflammation of the body tissue. Neurodegenerative diseases refer to diseases causing the breakdown of neural tissue and/or function. These both include local inflammatory responses and systemic inflammation. Examples of such diseases and conditions include: complications of organ transplantation including lung transplantation, including bronchitis, including obliterative bronchitis; chronic inflammatory disorders of the joints, including arthritis, rheumatoid arthritis, osteoarthritis and bone diseases associated with increased bone resorption; inflammatory bowel diseases such as ileitis, colitis, including ulcerative colitis, Barrett's syndrome, and Crohn's disease; inflammatory lung disorders such as asthma, adult respiratory distress syndrome, and chronic obstructive airway disease; inflammatory disorders of the eye including corneal dystrophy, trachoma, onchocerciasis, uveitis, sympathetic ophthalmitis and endophthalmitis; chronic inflammatory disorders of the gum, including gingivitis and periodontitis; tuberculosis; leprosy, inflammatory diseases of the kidney including ureinic complications, glomerulonephritis and nephrosis; inflammatory disorders of the skin including sclerodermatitis, psoriasis and eczema; inflammatory diseases of the central nervous system, including chronic demyelinating diseases of the nervous system, multiple sclerosis, AIDS-related neurodegeneration, Alzheimer's disease, infectious meningitis, encephalomyelitis, Parkinson's disease, Huntington's disease, amyotrophic lateral sclerosis and viral or autoimmune encephalitis; autoimmune diseases such as diabetes, including diabetic neuropathy, vascular complications of diabetes, and diabetes mellitus, immune-complex vasculitis, systemic lupus erythematosus (SLE); inflammatory diseases of the heart such as cardiomyopathy, ischemic heart disease, hypercholesterolemia, atherosclerosis, doxorubucin-induced cardiac dysfunction; as well as various other diseases with significant inflammatory components, including preeclampsia; chronic liver failure, brain and spinal cord trauma, and cancer. There may also be a systemic inflammation of the body, exemplified by gram-positive or gram negative shock, hemorrhagic or anaphylactic shock, or shock induced by cancer chemotherapy in response to pro-inflammatory cytokines.

The invention also includes a method of treating, preventing, or otherwise inhibiting reperfusion injury in a subject in need of treatment, prevention, or inhibition thereof. The method includes administering a peroxynitrite decomposition catalyst as disclosed herein in an amount sufficient to inhibit reperfusion injury in the subject. Reperfusion refers to the process whereby blood flow in the blood vessels is resumed after blood flow has been interrupted, such as occurs following constriction or obstruction of the vessel. Reperfusion is typically associated with ischemia and may result following a naturally occurring episode, such as a myocardial infarction or stroke, or during a surgical procedure where blood flow in vessels is purposely or unintentionally blocked off.

The subject in the above-mentioned methods can be, e.g., a mammal, e.g., a human, mouse, rat, dog, cat, horse, cow, pig, or non-human primate. Administration can be systemic or topical, and can be prophylactic or therapeutic.

The invention will be further described in the following examples, which do not limit the scope of the invention described in the claims.

Example 1

Synthesis of iron(III) meso-tetrakis(N,N-di-(2-(2-methoxyethoxy)ethyl)-imidazol-2-yl)porphyrin (6) ("FeTDPImP")

Figure 2A:
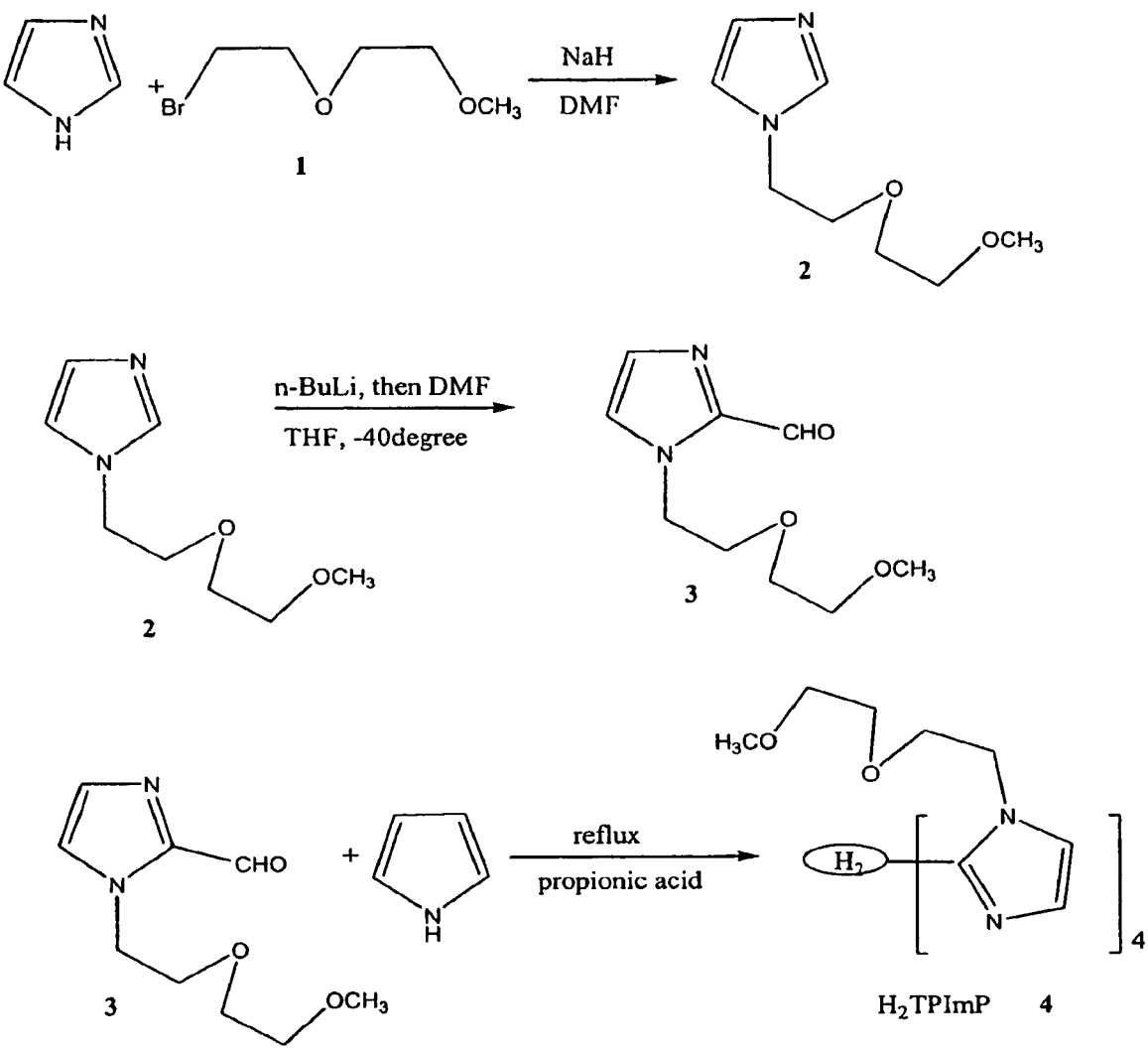
FIGS. 2A and 2B are a schematic representation of a synthesis for iron(III) meso-tetrakis(N,N-di-(2-(2-methoxyethoxy)ethyl)-imidazol-2-yl)porphyrin (FeTDPImP).
Figure 2B:
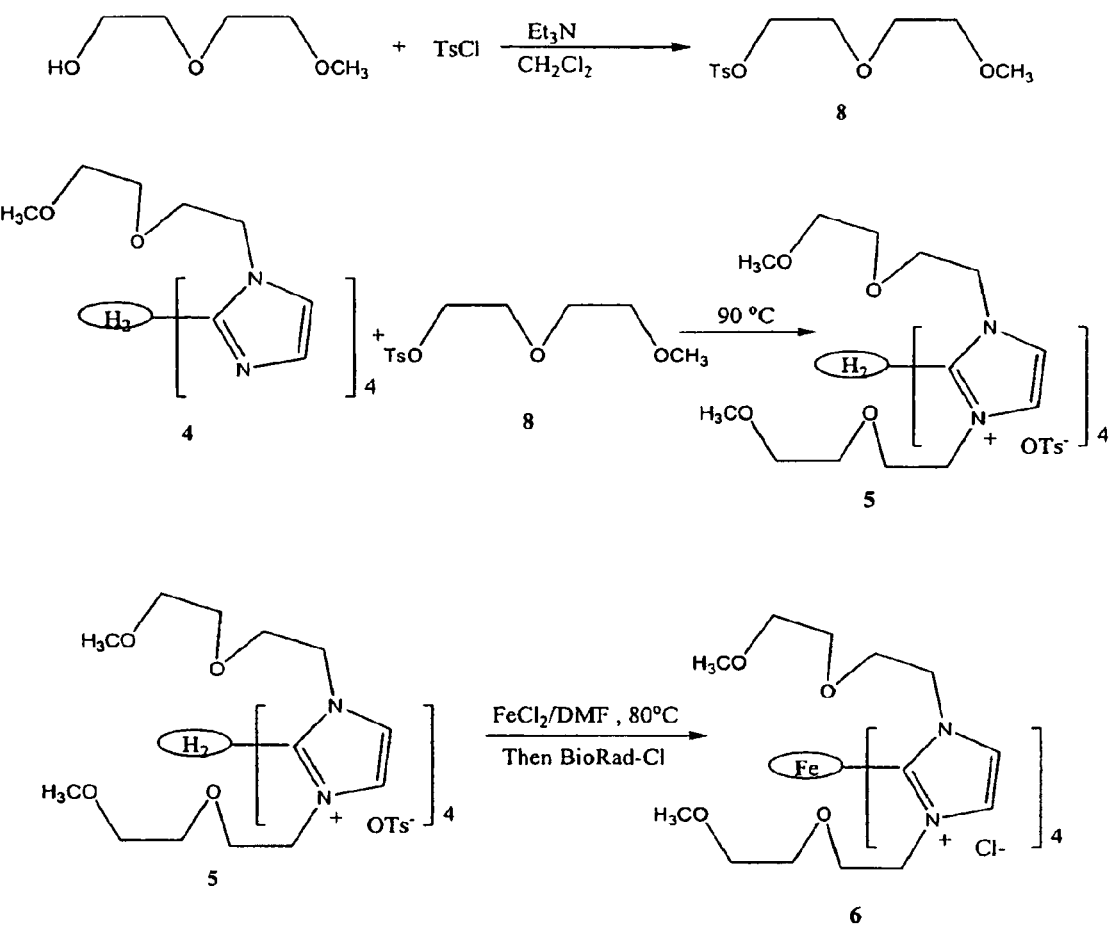

FeTDPImp (FW: 1626.2 g/mol) was synthesized from a starting imdizaole compound using the following synthetic scheme. The synthetic scheme is shown, along with structures of intermediate products, in FIGS. 2A and 2B.

1. Synthesis of N-(2-(2-methoxyethoxy)ethyl)-imidazole (2)

Imidazole 1 g (0.015 mol) was dissolved in dry DMF 50 mL under argon atmosphere. After a NaH mineral oil dispersion (60%) 0.68 g (0.017 mol) was added, the mixture was heated at 80° C. for 70 min. After cooling to room temperature, 1-Bromo-2-(2-methoxyethoxy)-ethane (1), 2.75 g (0.015 mol), was added, then stirred overnight. The reaction was poured into water, extracted by $CHCl_3$, washed by water, dried over $Na_2SO_4$, then dried (Rotavap) until an oily residue remained. The crude product was purified with silica gel flash column chromatography with an eluant of $CHCl_3$:$CH_3OH$=20:1. 1.69 g (70% yield) of the product (2) was obtained as a colorless oil. As an alternative to column chromatography, product (2) is purified by vacuum distillation.

2. Synthesis of N-(2-(2-methoxyethoxy)ethyl)-imidazole-2-carboxaldehyde (3)

1.30 g of (2) (0.008 mol) was dissolved in freshly distilled THF 35 mL under argon atmosphere, and the solution was cooled to −40° C. n-butyllithium 1.6M-hexane solution 5.6 mL (0.0088 mol) was added dropwise while the temperature was kept at −40° C. The mixture was then stirred at −40° C. for 30 min, after which dry DMF 1.28 mL (0.016 mol) was added. The contents were allowed to warm up to room temperature and stirred overnight. Sodium bicarbonate solution was added, then THF was dried (Rotavap), extracted by $CHCl_3$, dried over $Na_2SO_4$, and dried (Rotavap) until a light yellow oil was left. The product was purified by silica gel flash column chromatography, $CHCl_3$:$CH_3OH$=50:1. 0.861 g product (3) (57% yield) was obtained as a light yellow oil. As an alternative to column chromatography, the product (3) is purified by vacuum distillation.

3. Synthesis of meso-tetrakis(N-(2-(2-methoxyethoxy)ethyl)-imidazol-2-yl)porphyrin (4)

To 55 mL refluxing propionic acid was added 344 mg of (3) (1.8 mmol). Pyrrole was purified by passing through a short pad of alumina, after which 0.134 mL (1.9 mml) was added dropwise slowly over a period of 10 minutes. The reaction was kept refluxing for 4 hours, then cooled to room temperature and wrapped with aluminum foil to stir open to air overnight. Propionic acid was distilled under vacuum and the black residue was dissolved in acetone 3 mL and concentrated HCl 3 mL. After sitting for 5 min, it was dried (Rotavap) at 40° C., then dissolved in ($CHCl_3$+$Et_3N$) and washed by water, then dried on Rotavap. The product was purified on alumina column with $CHCl_3$: $CH_3OH$=100:1. After recrystallization ($CHCl_3$/$Et_2O$), 88 mg of (4) (21% yield) was obtained as dark purple solid.

4. Synthesis of 2-(2-methoxyethoxy)ethyl tosylate (8)

2-(2-methoxyethoxy)ethanol 3.06 g (25.6 mmol) and TsCl 6.25 g (32.78 mmol) were dissolved in freshly distilled $CH_2Cl_2$, triethylamine (7.1 mL) was added then stirred under argon overnight. Saturated sodium bicarbonate solution (40 mL) and ethyl acetate (100 ml) were added. The organic layer was washed with 1N potassium bisulfate (80 mL), then saturated sodium bicarbonate solution (80 mL), dried over $Na_2SO_4$, then dried on rotavap to produce an oil. The product was purified on silica gel flash column with $CHCl_3$:EtOAc=5:1. Product (8) 6.77 g (97% yield) was obtained as a colorless oil. Solvents such as $CH_3CN$ and THF may be used instead of $CH_2Cl_2$ in the synthesis of compound 8.

5. Synthesis of meso-tetrakis(N,N-di-(2-(2-methoxyethoxy)ethyl)-imidazol-2-yl)porphyrin (5)

Under inert atmosphere, to 73 mg of (4) was added 2.0 mL of (8). The mixture was heated at 90° C. overnight. A minimum volume of $CHCl_3$ was added to dissolve the mixture, then $Et_2O$ was added. The suspension was filtered through a pad of celite and washed with more $Et_2O$. The dark porphyrin on celite was washed off with methanol and dried (Rotavap). 127 mg of porphyrin (5) (80% yield) was obtained as a dark purple solid. $\lambda_{max}$=413 nm in pH 7.4 PBS. It was characterized by $^1$H-NMR and electrospray spectroscopy. As an alternative to the tosylate (8), the bromide (1) may be used to alkylate the porphyrin.

6. Synthesis of iron(III) meso-tetrakis(N,N-di-(2-(2-methoxyethoxy)ethyl)-imidazol-2-yl)porphyrin (6)

127 mg of porphyrin (5) (0.061 mmol) dissolved in 7 mL dry DMF under inert atmosphere. 8 mg $FeCl_2$ anhydrous (0.061 mmol) was added and was heated at 80° C. for 4 hours. The completion of metallation was monitored by UV-Vis spectroscopy and 8 mg of $FeCl_2$ was added once or twice until the reaction was complete. After cooling to room temperature, ether was added to precipitate the porphyrin out. The precipitate was filtered through a short pad of Celite, washed with ether, then collected by washing off with methanol then dried (Rotavap). The resulting solid was stirred with Bio-Rad resin (Cl-form) then filtered through a short pad of resin and dried under vacuum. The solid was further dissolved in methanol and filtered through a short pad of Celite, then dried under vacuum. 67 mg of iron porphyrin (6) (70% yield) was obtained as a dark purple solid. The product was further free dried under vacuum to give a powdery solid. $\lambda_{max}$=403 nm in pH 7.4 PBS. The product was characterized by LC-MS and $^1$H-NMR.

Example 2

Synthesis of (iron(III) meso-tetrakis(N,N-dicarboxymethyl)-imidazol-2-yl)porphyrin) ("FeTDCMImP")

Figure 3:
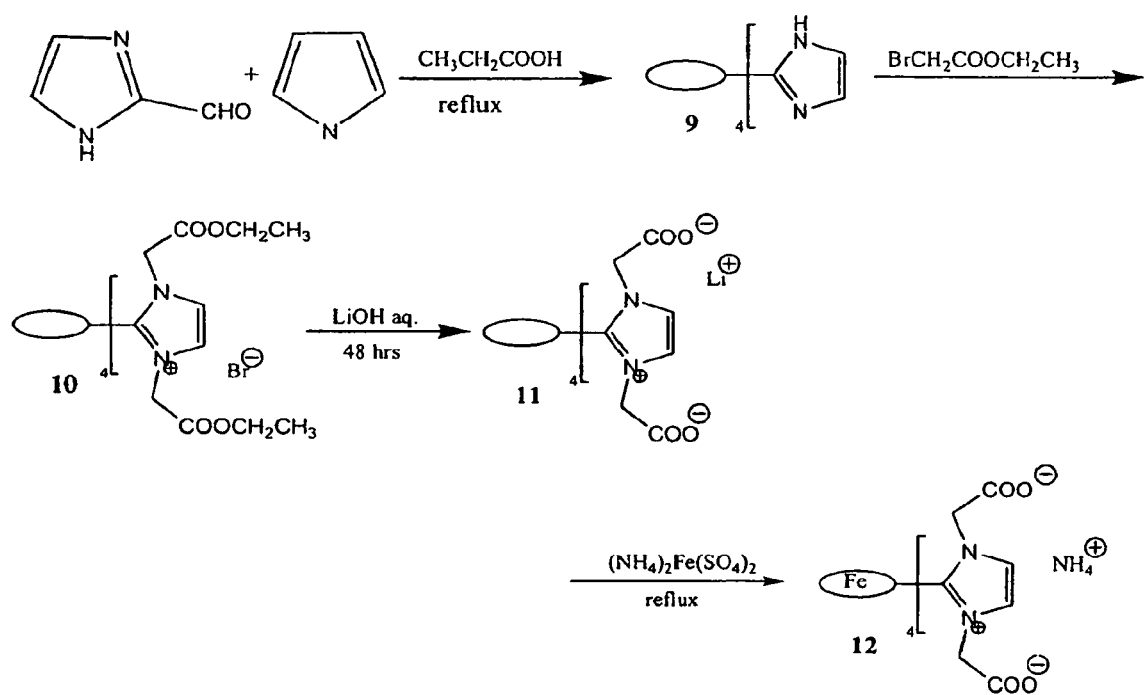
FIG. 3 is a schematic representation of a synthetic scheme for iron(III) meso-tetsakis(N,N-dicarboxymethyl)-imidazol-2-yl)porphyrin.

FeTDCMImP was synthesized from a starting imdizaole compound using the following synthetic scheme, which is shown along with structures of intermediate products, in FIG. 3.

1. Synthesis of H₂TImP (meso-tetra-imidazol-2-yl-porphyrin) (9)

H₂TImP was synthesized using one of two different pathways, that described in Milgrom et al., *Tetrahedron*, 1996, 29, 9877-9890, or that described in Milgrom et al., *Journal of Molecular Electronics*, 1991, 7, 95-100.

To a refluxing 125 mL propionic acid, -2.4 g (0.025 mol) of imidaxole-2-carboxaldehyde was added, then 1.675 g (0.025 mol) of pyrrole was added slowly. After refluxing for 1.5 hours, the reaction was cooled to room temperature, then placed in a refrigerator for 2 hours. The mixture was filtered, washed with chloroform, acetone, methanol and water to obtain 51 mg (1.5%) of purple solid as the product. The UV absorption and ¹H-NMR spectroscopy was consistent with the reported compound (Milgrom, 1991). MALDI-TOF: m/z=576 (M+H)

2. Synthesis of meso-tetrakis(N,N-diethylacetyl)-imidazol-2-yl)porphyrin (10)

Under inert atmosphere, to 60 mg of (9) (0.107 mmol) in 15 mL of anhydrous DMF was added 4.5 mL of ethyl bromoacetate. The mixture was heated at 70° C. for 5 hours and then stirred at room temperature overnight. 60 mL of Et₂O was added, after which the mixture was cooled in at 4° C. for 30 min. The dark porphyrin precipitate was filtered to obtain 104 mg of product 10 as a dark purple solid. The product was characterized by ¹H-NMR and electrospray mass spectroscopy.

3. Synthesis of meso-tetrakis(N,N-dicarboxymethyl)-imidazol-2-yl)porphyrin (11)

Porphyrin 10 91 mg (0.058 mmol) was dissolved in 3 mL water, then 0.1 M LiOH aqueous solution 2.5 mL (0.24 mmol) was added dropwise. After stirring at room temperature for 48 hours, water was removed (Rotavap). The residue was dissolved in methanol, then solid salts were filtered offend the filtrate was dried (Rotavap). The dark porphyrin was dissolved in 15 mL methanol and 10 mL of ethyl ether was added to precipitate it out. After filtration, product 11 was obtained as 65.3 mg dark purple solid with near quantitative yield. Compound II was characterized by electrospray mass spectroscopy and ¹H-NMR. $\lambda_{max}$=410 nm in water.

4. Synthesis of iron(III) meso-tetrakis(N,N-dicarboxymethyl)-imidazol-2-yl)porphyrin (12)

20 mg of porphyrin 11 (0.019 mmol) dissolved in 5 mL water. 78 mg of ferrous ammonium sulfate (0.19 mmol) was added and the mixture refluxed for 15 hours. After cooling to room temperature, the dark purple porphyrin precipitate was filtered and washed with water to obtain 17.2 mg of iron porphyrin (12) (82% yield). $\lambda_{max}$=395 nm in pH 7.4 PBS. LC-MS characterization of the product revealed one major component with the desired molecular mass of 1088 (without counterion).

Example 3

Determination of Peroxynitrite Decomposition Catalysis

A high rate of peroxynitrite decomposition is an important indicator of biological activity in vitro and in vivo. The rates of reaction between peroxynitrite and various iron porphyrins were measured at several different concentrations of catalyst in phosphate buffer (pH=7.4). The ONOO⁻ decay rate ($M^{-1}s^{-1}$) for FeTDMImP was determined to be $1.0 \times 10^6 M^{-1}s^{-1}$, and the $k_{cat}$ for FeTDCMImP was measured at $4.6 \times 10^5$. In the same studies the decay rates for the iron porphyrins FeTDMImP, FeTDCMImP, FeTDPImP (see, e.g., U.S. Pat. No. 6,448,239) were $1.1 \times 10^6$, $4.6 \times 10^5$ and $1.9 \times 10^6$, respectively.

Example 4

Stopped-Flow Spectrometry of Peroxynitrite Decomposition catalyzed by FeTDCIImP (12)

Figure 4:
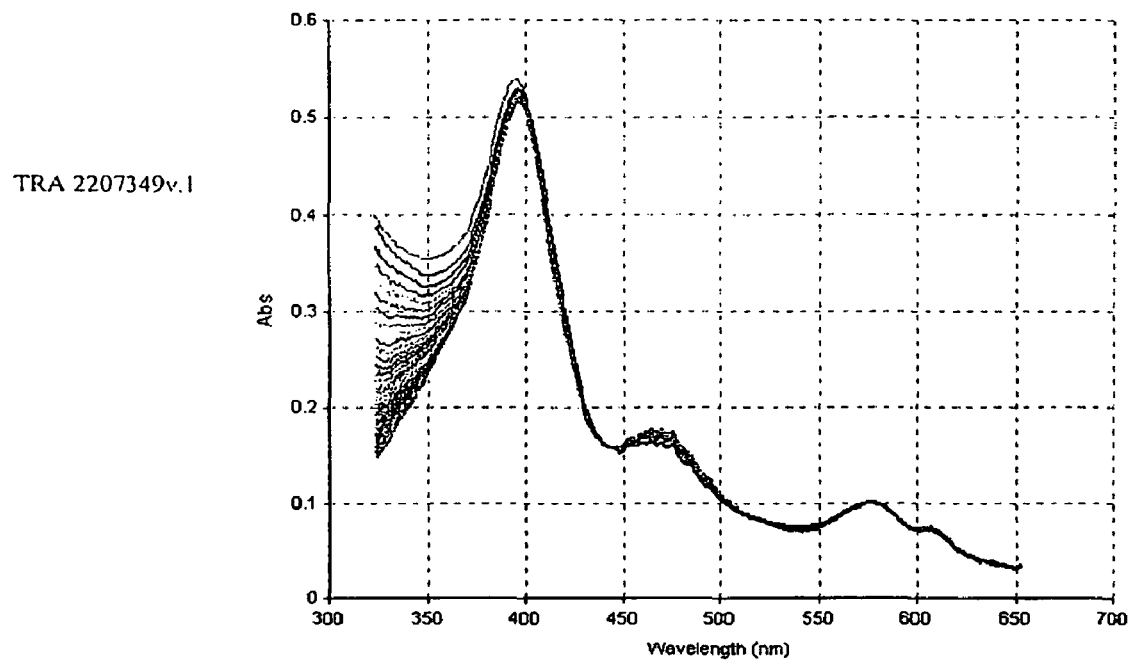
FIG. 4 is stopped-flow spectroscopy of peroxynitrite decomposition catalyzed by FeTDCImP (12). (A) diode array scan of 10 µM (12) in pH 7.4 PBS mixed with 600 µM, t=2 s; (B) decay of peroxynitrite monitored at 324 nm, condition that same as in A. It was fitted into a first order kinetics model using KinetAssyst software. Data was average of four parallel experiments.
Figure 4:
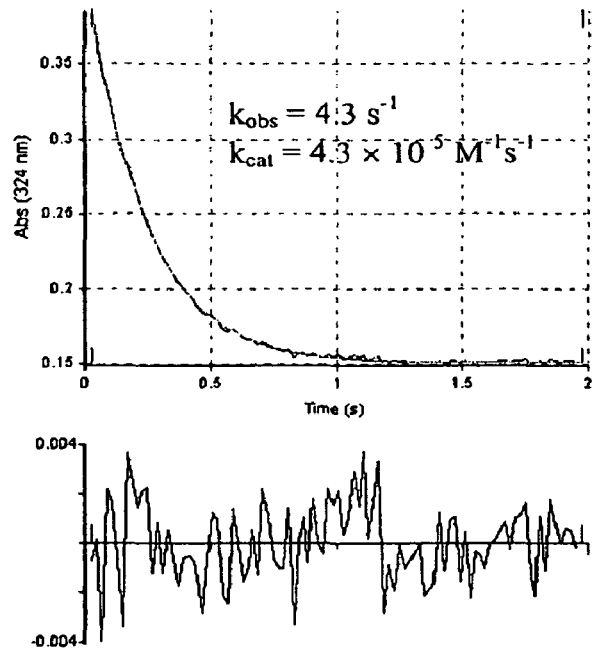

FeTDCMImP (12) was demonstrated to be an efficient peroxynitrite decomposition catalyst in vitro with a second order rate constant of $4.3 \times 10^5 M^{-1}s^{-1}$) in pH 7.4 phosphate buffer as detected by stropped-flow spectrometer where the absorption of peroxynitrite at 324 nm was monitored (FIG. 4). This rate constant placed it right in between cationic FeTM-4-PyP ($1.8 \times 10^6$) and anionic FeTMPS ($1.23 \times 10^5 M^{-1}s^{-1}$). It was rationalized that the electron-withdrawing cationic feature elevated its catalytic activity as compared to anionic porphyrins, while its electron-donating anionic feature lowered its catalytic activity as compared to cationic porphyrins. This combination of cationic and anionic motifs was expected to possess both the advantage of cationic motif in catalytic activity and the advantage of anionic motif in tissue distribution.

Other Embodiments

It is to be understood that while the invention has been described in conjunction with the detailed description thereof, the foregoing description is intended to illustrate and not limit the scope of the invention, which is defined by the scope of the appended claims. For example, substituted-pyridyl derivatives, particularly those including PEG substituents, are particularly advantageous as peroxynitrite decomposition catalysts. Other aspects, advantages, and modifications are within the scope of the following claims.

What is claimed is:

1. A compound having Formula III

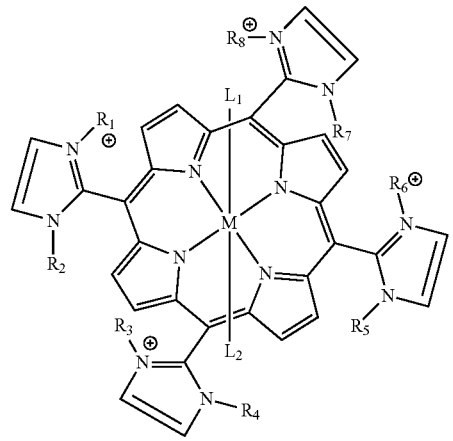

Formula III or a pharmaceutically acceptable base or acid addition salt, hydrate, ester, solvate, stereoisomer, or mixtures thereof, wherein at least one of $R_1$, $R_2$, $R_3$, $R_4$, $R_5$, $R_6$, $R_7$, or $R_8$ is $CH_2CH_2OCH_2CH_2OCH_3$ or $CH_2COO^-$, the remaining $R_1$, $R_2$, $R_3$, $R_4$, $R_5$, $R_6$, $R_7$, or $R_8$ are hydrogen, $L_1$ and $L_2$ are, independently, absent, halide, oxo, $OH_2$, hydroxo, CN, $OPO_3H$ or alcohol; and M is Fe.

* * * * *